United States Patent
Mingione et al.

(10) Patent No.: US 10,549,078 B2
(45) Date of Patent: Feb. 4, 2020

(54) ANTISEPTIC APPLICATOR

(71) Applicant: CAREFUSION 2200, INC, San Diego, CA (US)

(72) Inventors: Louis P. Mingione, Chicago, IL (US); Satish Degala, Arlington Heights, IL (US); Kenneth Bruce Thurmond, Deer Park, IL (US); Andre M. Rustad, Etiwanda, CA (US); Michael McMahon, Yorba Linda, CA (US); Benjamin T. Krupp, Wyoming, OH (US); Charlie Beuchat, Anaheim Hills, CA (US); Maya P. Singh, Bardonia, NY (US)

(73) Assignee: CAREFUSION 2200, INC, San Diego, CA (US)

( * ) Notice: Subject to any disclaimer, the term of this patent is extended or adjusted under 35 U.S.C. 154(b) by 185 days.

(21) Appl. No.: 15/882,539

(22) Filed: Jan. 29, 2018

(65) Prior Publication Data

US 2018/0147397 A1    May 31, 2018

Related U.S. Application Data

(63) Continuation of application No. 14/595,084, filed on Jan. 12, 2015, now abandoned.

(51) Int. Cl.
*A61M 35/00* (2006.01)
*A61L 2/00* (2006.01)

(52) U.S. Cl.
CPC ......... *A61M 35/003* (2013.01); *A61L 2/0005* (2013.01); *A61L 2/0088* (2013.01)

(58) Field of Classification Search
CPC .. A61M 35/003; A61M 35/006; A61M 11/00; A61L 2/0005; A61L 2/0088; B43K 5/14; B43K 5/18; A45D 34/042; A45D 34/04; A45D 2200/1018; A46B 11/0027; B43M 11/06
See application file for complete search history.

(56) References Cited

U.S. PATENT DOCUMENTS

| | | |
|---|---|---|
| 3,757,782 A | 9/1973 | Aiken |
| 4,415,288 A | 11/1983 | Gordon et al. |
| 4,498,796 A | 2/1985 | Gordon et al. |
| 5,288,159 A | 2/1994 | Wirt |
| 5,308,180 A | 5/1994 | Pournoor et al. |
| 5,435,660 A | 7/1995 | Wirt |
| 5,445,462 A | 8/1995 | Johnson et al. |
| 5,658,084 A | 8/1997 | Wirt |
| 5,769,552 A | 6/1998 | Kelley et al. |

(Continued)

FOREIGN PATENT DOCUMENTS

WO    WO 2016/094716 A1    6/2016

*Primary Examiner* — Adam Marcetich
*Assistant Examiner* — Jessica R Arble
(74) *Attorney, Agent, or Firm* — Arent Fox LLP

(57) ABSTRACT

An applicator assembly includes at least one ampoule formed of a frangible material and containing liquid to be applied, a body having a proximal end, a distal end, and an interior portion defining a chamber adapted to receive the at least one ampoule, an application member attached to the distal end of the body, an actuator projecting from the body operable to fracture the at least one ampoule, a trench formed in a surface of the body, and a vent disposed through a surface of the trench.

18 Claims, 20 Drawing Sheets

(56) References Cited

U.S. PATENT DOCUMENTS

| | | |
|---|---|---|
| 5,772,346 A | 6/1998 | Edwards |
| 5,791,801 A | 8/1998 | Miller |
| 5,927,884 A | 7/1999 | Kao |
| 6,371,675 B1 | 4/2002 | Hoang et al. |
| 6,488,665 B1 | 12/2002 | Severin et al. |
| 6,729,786 B1 * | 5/2004 | Tufts ............... A45D 34/04 401/132 |
| 6,916,133 B2 | 7/2005 | Hoang et al. |
| 7,201,525 B2 | 4/2007 | Mohiuddin |
| 8,556,529 B2 | 10/2013 | Law et al. |
| 2004/0179889 A1 | 9/2004 | Tufts et al. |
| 2004/0254561 A1 | 12/2004 | Stenton |
| 2006/0039742 A1 | 2/2006 | Cable, Jr. et al. |
| 2007/0231051 A1 | 10/2007 | Flores et al. |
| 2008/0219750 A1 | 9/2008 | Siegel |
| 2008/0298879 A1 | 12/2008 | Chesak et al. |
| 2010/0168638 A1 | 7/2010 | Korogi et al. |
| 2016/0228686 A1 | 8/2016 | Dombrowski et al. |

* cited by examiner

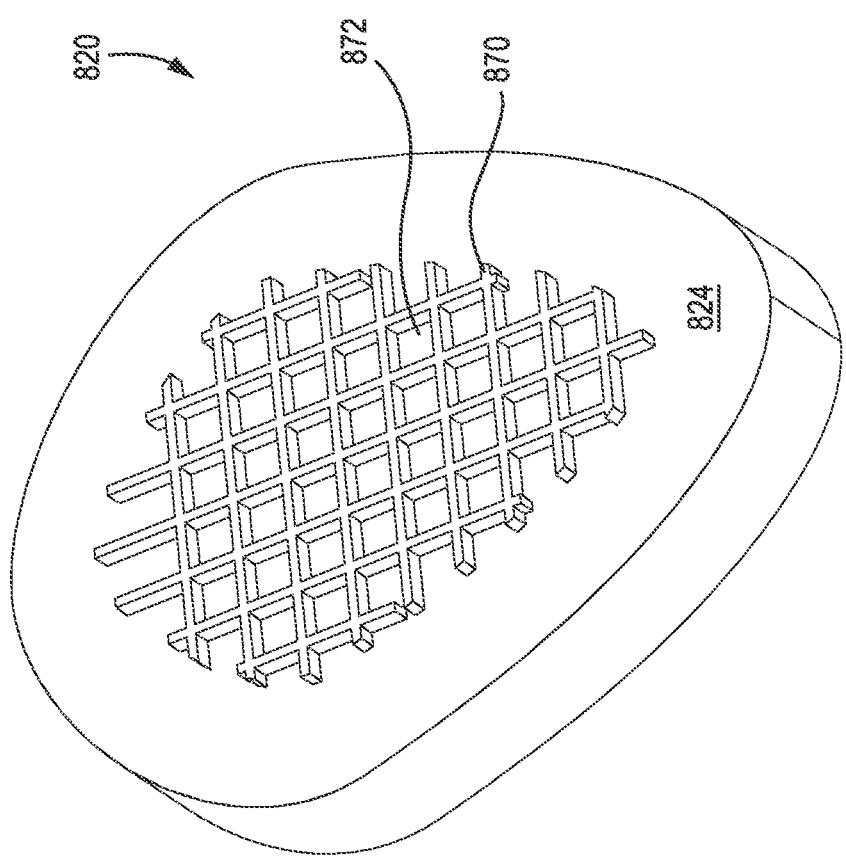

ANTISEPTIC APPLICATOR

CROSS-REFERENCE TO RELATED APPLICATION

This application is a Continuation of U.S. patent application Ser. No. 14/595,084, filed Jan. 12, 2015. The disclosure of the prior application is hereby incorporated in its entirety by reference.

BACKGROUND

Field

The present disclosure relates to antiseptic applicators and methods of use thereof, and more particularly, to an antiseptic applicator that uses a compressive force to actuate release of a sealed solution, preferably an antimicrobial solution, from an ampoule.

Description of Related Art

Antiseptic applicators for the preparation of a patient prior to surgery, for example, are known and common in the prior art. Conventional applicators rely on various means of actuation to release a self-contained reservoir of antimicrobial solution for sterilization of the patient's skin. For example, a number of applicators are designed with a puncturing means. These applicators typically include a head with a spike, for example, and a sealed container or cartridge. A push or screw motion is employed to axially translate the head toward the sealed container so that the spike may pierce the sealed container and effectuate the release of the solution contained therein. Some examples of applicators using a puncturing means include U.S. Pat. Nos. 4,415,288; 4,498,796; 5,769,552; 6,488,665; and 7,201,525; and U.S. Pat. Pub. No. 2006/0039742.

Other conventional applicators rely on fracturing an internally situated frangible container or ampoule through the application of a one-way directional force or a localized application of pressure. The directional force is typically applied longitudinally to one end of the ampoule by a pushing motion designed to force the ampoule to fracture under a compressive stress, sometimes at a predetermined area of stress concentration. Alternatively, a pressure may be applied to a localized section of the ampoule through a squeezing motion designed to crush a section of the frangible ampoule in order to release the antimicrobial solution contained therein. Some examples of applicators using frangible ampoules in the manner discussed above include U.S. Pat. Nos. 3,757,782; 5,288,159; 5,308,180; 5,435,660; 5,445,462; 5,658,084; 5,772,346; 5,791,801; 5,927,884; 6,371,675; and 6,916,133. All of the above listed Patent Application Publication and U.S. patents are hereby expressly incorporated by reference herein.

However, in the above-listed applicators, it may be difficult for the user to operate the devices to release the solution. For example, in conventional applicators the user may accidentally block the vent hole during use. Further, the actuators of conventional applicators may be difficult to actuate and/or the bodies of the applicator may be difficult to comfortably handle. Thus, there is a need in the art for an antiseptic applicator that is easier to operate.

SUMMARY

In accordance with aspects of the present invention, an applicator assembly may include at least one ampoule formed of a frangible material and containing liquid to be applied; a body having a proximal end, a distal end, and an interior portion defining a chamber adapted to receive the at least one ampoule; an application member attached to the distal end of the body; an actuator projecting from the body operable to fracture the at least one ampoule; a trench formed in a surface of the body; and a vent disposed through a surface of the trench.

It will become readily apparent to those skilled in the art from the following detailed description, wherein it is shown and described only exemplary configurations of an applicator assembly. As will be realized, the invention includes other and different aspects of an applicator and assembly and the various details presented throughout this disclosure are capable of modification in various other respects, all without departing from the spirit and scope of the invention. Accordingly, the drawings and the detailed description are to be regarded as illustrative in nature and not as restrictive.

BRIEF DESCRIPTION OF THE DRAWINGS

FIG. 20 is a perspective view of an embodiment of an application member for use with an antiseptic applicator assembly, in accordance with aspects of the present invention.

DETAILED DESCRIPTION

Figure 1:
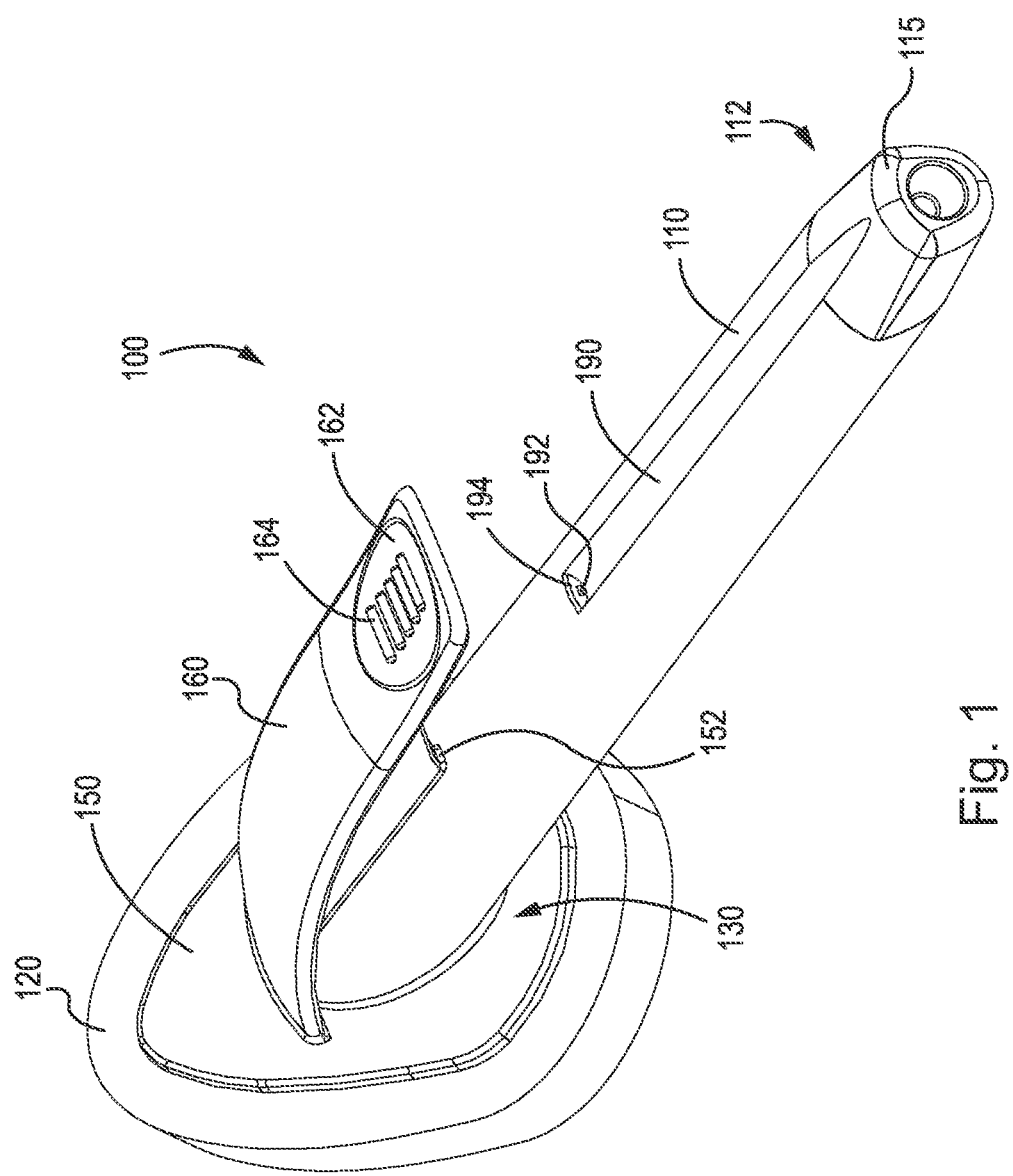
FIG. 1 is a perspective view of an antiseptic applicator assembly, in accordance with aspects of the present invention.

Various aspects of an antiseptic applicator assembly may be illustrated by describing components that are coupled, attached, and/or joined together. As used herein, the terms "coupled", "attached", and/or "joined" are used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements present.

Relative terms such as "lower" or "bottom" and "upper" or "top" may be used herein to describe one element's relationship to another element illustrated in the drawings. It will be understood that relative terms are intended to encompass different orientations of an antiseptic applicator assembly in addition to the orientation depicted in the drawings. By way of example, if an antiseptic applicator assembly in the drawings is turned over, elements described as being on the "bottom" side of the other elements would then be oriented on the "top" side of the other elements. The term "bottom" can therefore encompass both an orientation of "bottom" and "top" depending on the particular orientation of the apparatus.

Various aspects of an antiseptic applicator assembly may be illustrated with reference to one or more exemplary embodiments. As used herein, the term "exemplary" means "serving as an example, instance, or illustration," and should not necessarily be construed as preferred or advantageous over other embodiments of an antiseptic applicator assembly disclosed herein.

The term "about" as used herein means ±10%, more preferably ±5%, and still more preferably ±1% of the provided value.

Figure 2:
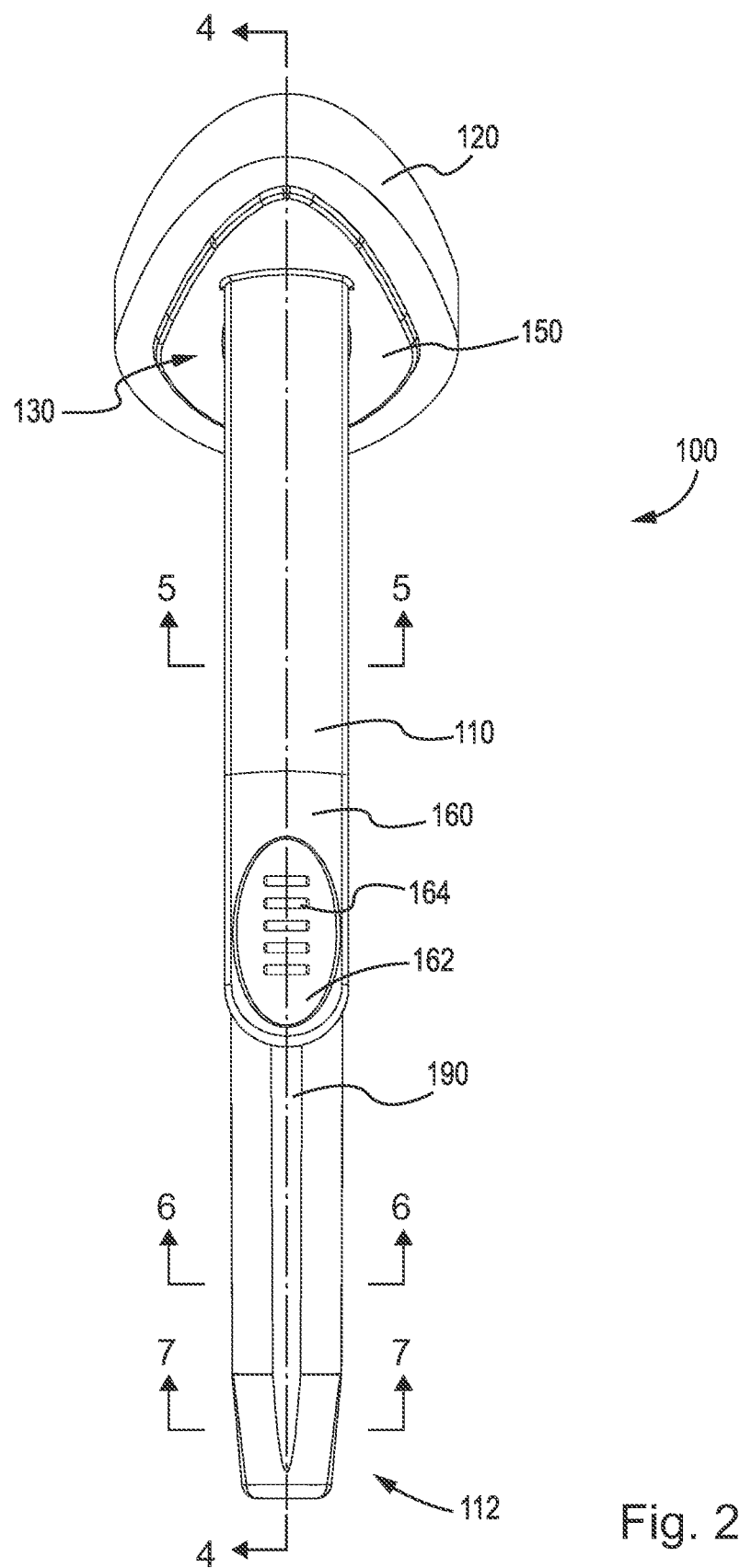
FIG. 2 is a top view of the antiseptic applicator assembly of FIG. 1.
Figure 3:
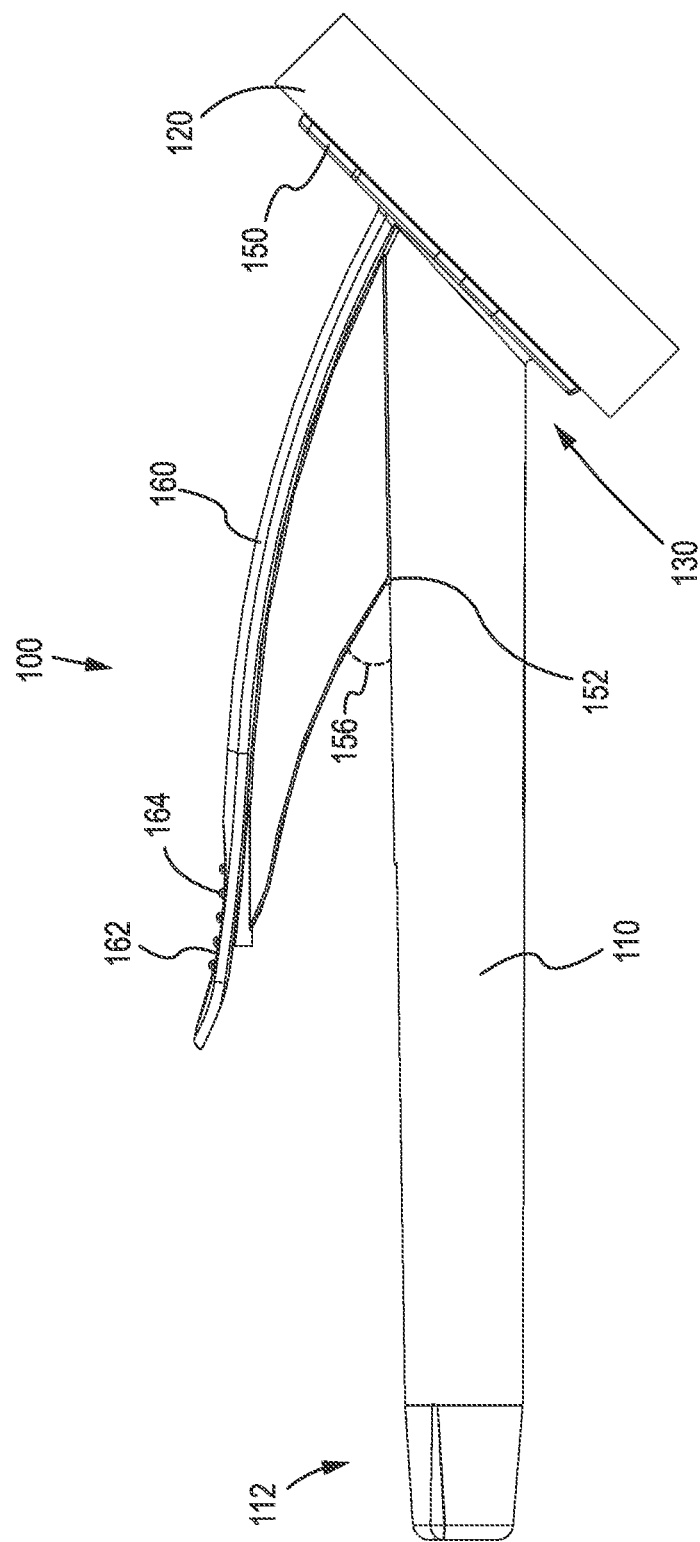
FIG. 3 is a side view of the antiseptic applicator assembly of FIG. 1.
Figure 4:
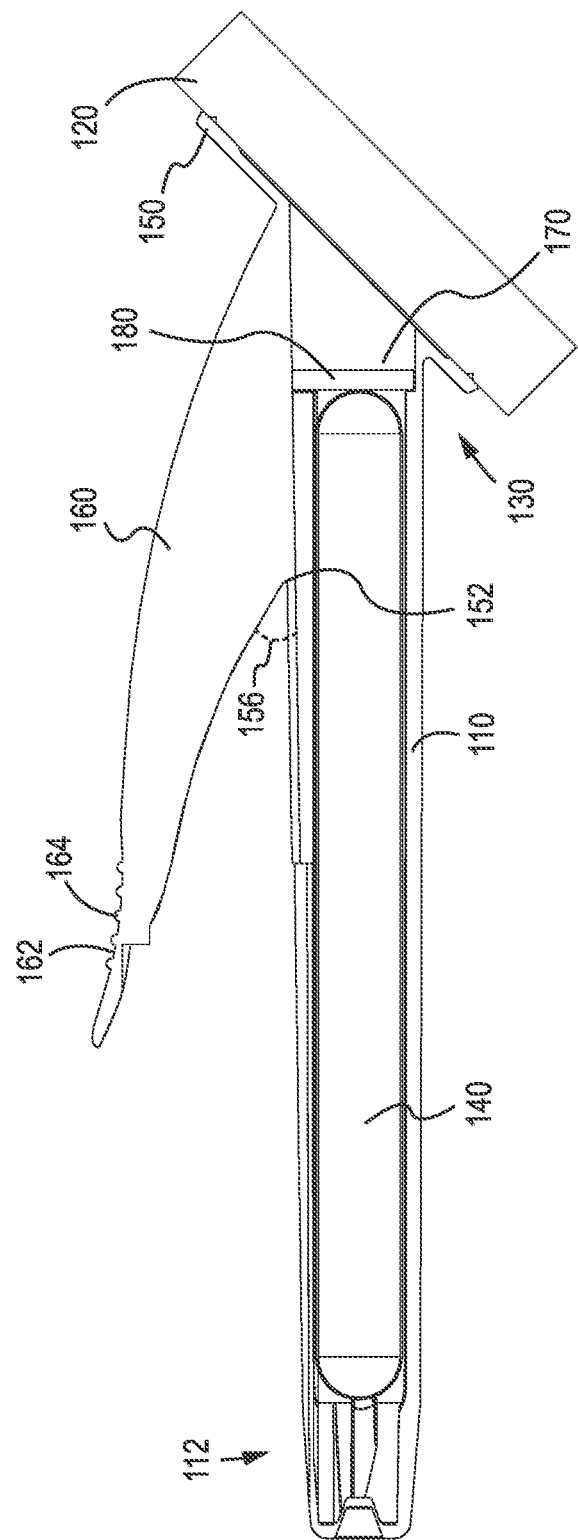
FIG. 4 is a cross section view of antiseptic applicator of FIG. 1 taken along line 4-4 of FIG. 2.
Figure 5:
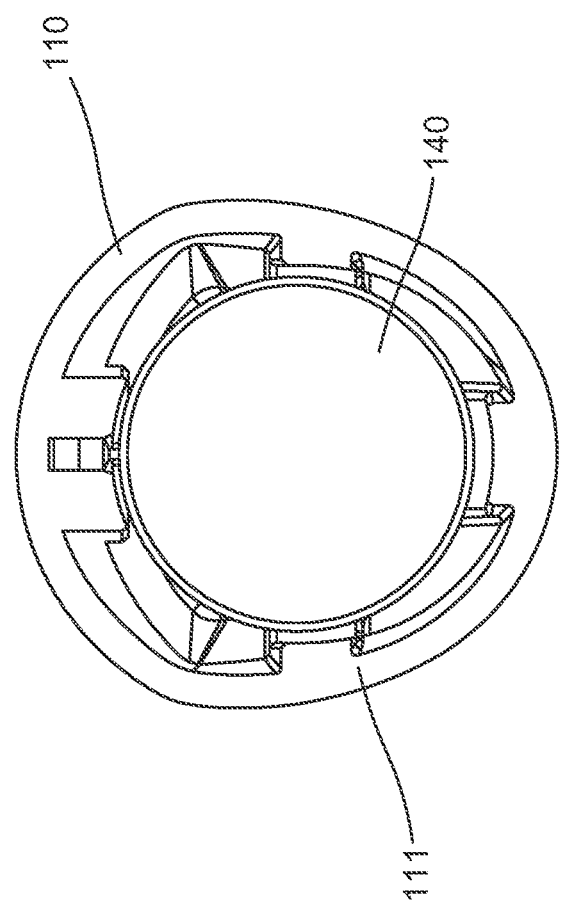
FIG. 5 is a cross section view of antiseptic applicator of FIG. 1 taken along line 5-5 of FIG. 2.
Figure 6:
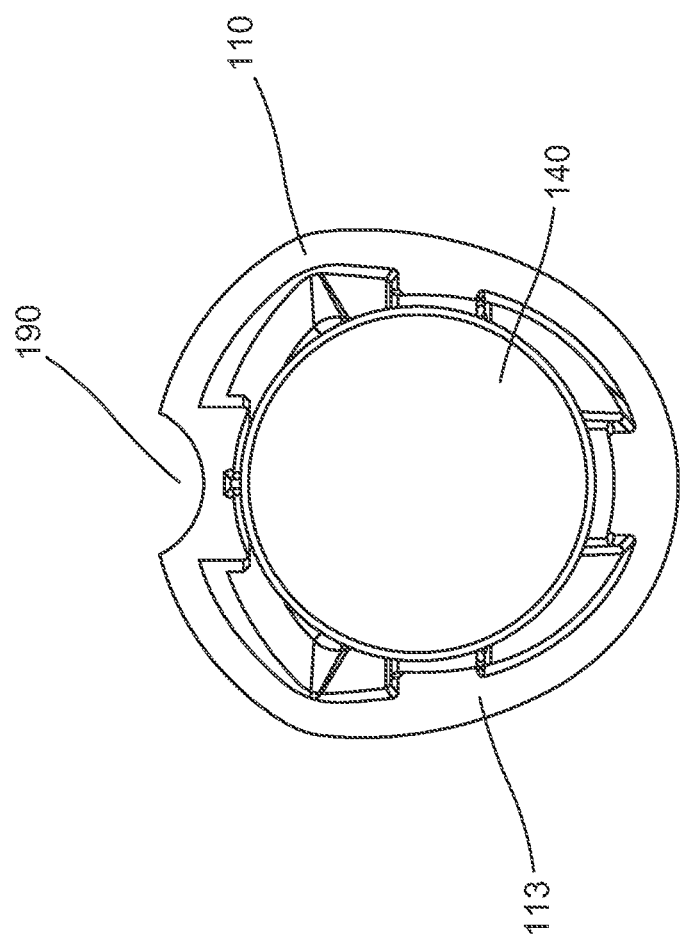
FIG. 6 is a cross section view of antiseptic applicator of FIG. 1 taken along line 6-6 of FIG. 2.
Figure 7:
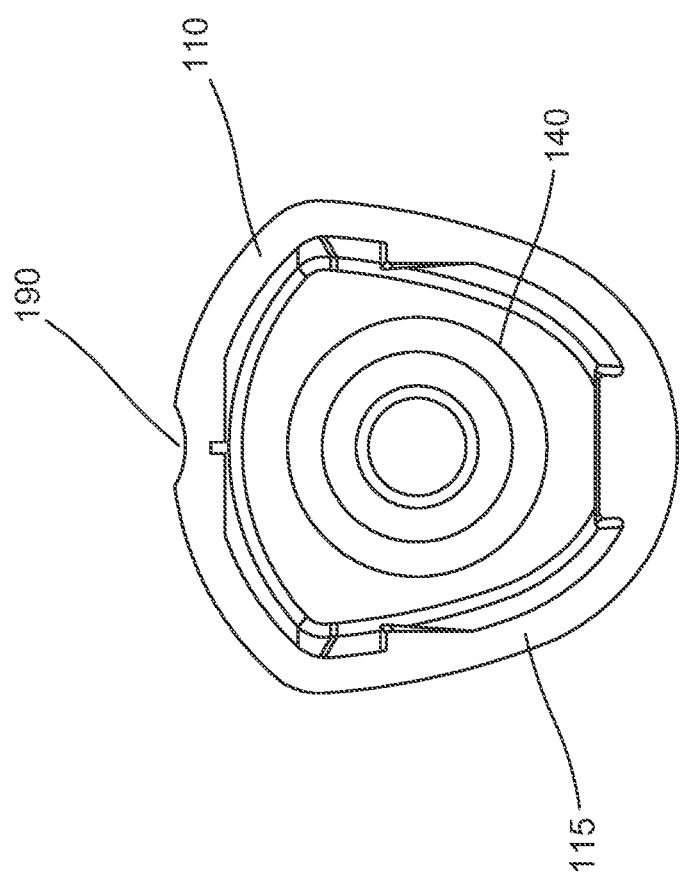
FIG. 7 is a cross section view of antiseptic applicator of FIG. 1 taken along line 7-7 of FIG. 2.

FIG. 1 shows a perspective view of an antiseptic applicator assembly 100 in accordance with aspects of the present invention. FIG. 2 shows a top view of the applicator assembly 100. FIG. 3 shows a side view of the applicator assembly of 100. FIG. 4 shows a cross section view of the applicator assembly 100 taken alone line 4-4 of FIG. 2. FIG. 5 shows a cross section of the applicator assembly 100 taken along line 5-5 of FIG. 2. FIG. 6 shows a cross section of the applicator assembly 100 taken along line 6-6 of FIG. 2. FIG. 7 shows a cross section of the applicator assembly 100 take along line 7-7 of FIG. 2.

As shown in FIGS. 1-4, the antiseptic applicator assembly 100 may comprise a substantially hollow body 110, which may be cylindrical in shape, an application member 120 mounted to a distal end portion 130 of the body 110, and one or more ampoules 140 (FIG. 4) received within the body 110. The terms "container" and "ampoule" are used interchangeably herein. The ampoules 140 may be cylindrical or tubular in shape to position the ampoules concentrically into the body 110. In other aspects of the present invention, the body may be any variety of shapes and the container can be any variety of shape that corresponds to (e.g., is congruent to) the particular shape of the body. In a preferred embodiment, the cross section shape of the body may vary along the length in the manner described in detail below. In an aspect of the present invention the applicator body may be formed of a single piece or it may be made of multiple pieces combined together.

As shown in FIGS. 1 and 2, the application member 120 may have a teardrop shape. The application member 120 may be formed from a foam sponge material, for example, or any suitable material that allows the controlled application of the contained solution from the ampoules 140 to a surface external to the applicator 100. The material chosen may be porous with a particular soak rate, for example, or may be provided with structural features, including slits or apertures, to direct and control the flow rate of the solution through the application member 120. The body 110 may be configured to have a mounting flange 150 at the distal end portion. The mounting flange 150 provides a surface for affixing the application member 120 to the body 110. In an aspect, the foam may be attached in any acceptable manner known in the relevant art, such as providing a novonette backing to the application member, which allows the application member to be ultrasonically welded to the body of the applicator.

The ampoule 140 is preferably a self-contained structure, formed of a suitable material that is fracturable upon application of sufficient force. Preferably, the ampoule 140 is formed of glass, although other materials such as frangible plastic are within the scope of the present invention. The wall of the ampoules may have a thickness sufficient to contain the desired liquid during transport and storage, yet allow the container to be fractured upon the application of localized pressure. The ampoule 140 may contain medicaments, chemical compositions, cleansing agents, cosmetics, or the like. For example, the ampoule 140 may be filled with antiseptic compositions (e.g., compositions comprising one or more antiseptic molecules) preferably an antimicrobial liquid or gel composition, such as a chlorhexidine gluconate solution, octenidine dihydrochloride solution, or a povidone iodine (PVP-I) alcohol gel solution, for antiseptic application to a patient prior to surgery. The ampoule 140 may be designed to withstand various heat and chemical sterilization techniques, which may be performed sequentially with a solution filling process, in accordance with techniques that are well known in the art.

The antiseptic solution may comprise an alcoholic, non-alcoholic, or combination solvent. That is, the solution may be aqueous, alcoholic, or hydroalcoholic. For example, the alcoholic solvent may be selected from the group consisting of ethanol, isopropanol, and n-propanol. The amount of solvent may be from about 40% v/v to about 90% v/v, more preferably about 50% v/v to about 80% v/v, and still more preferably about 60% v/v to about 70% v/v.

The container may contain antiseptic solution of a sufficient amount to be applied to a desired surface and have an antimicrobial effect on the desired surface. In one aspect, the desired surface is a patient's skin. It will be appreciated that the amount of antiseptic solution needed to have an antimicrobial effect on a desired surface to which the antiseptic is applied may vary. In one aspect the amount of antiseptic solution needed is 0.01-100 ml. More preferably, the amount of antiseptic solution is about 0.5-60 ml and still preferably about 0.5-30 ml. Examples include 0.67, 1.0, 1.5, 3.0, 10.5, and 26.0 ml of antiseptic solution. However, it will be appreciated that any amount of the antiseptic solution that has an antimicrobial effect on a desired surface may be utilized with the applicator and method. Two ampoules (or more) may be implemented, for example when higher volumes of antiseptic solution are desired. Thus, with two ampoules, the overall amount of antiseptic solution in the applicator 100 may be divided between the two ampoules. For example, for a 26.0 ml applicator, each ampoule may include 13.0 ml of antiseptic solution. The same principle may be implemented for any amount of solution, e.g., two ampoules of 0.5 ml together totaling 1.0 ml of solution, two ampoules of 1.5 ml together totaling 3.0 ml of solution, and so forth. It is also possible to divide the amount of solution unequally, if desired (i.e., such that one ampoule has more solution than the other ampoule). Furthermore, more than two ampoules may be implemented. For example, three, four, or more ampoules may be implemented. In these cases the amount of solution may be divided between as many ampoules as are present.

Suitable antiseptic molecules include bis-(dihydropyridinyl)-decane derivatives, octenidine salts, cationic surfactants, biguanides, and generally cationic antiseptic molecules. Preferred antiseptic agents include octenidine dihydrochloride and chlorhexidine gluconate. The concentration of the cationic antiseptic in hydroalcoholic solution may vary depending on the specific cationic antiseptic species used or the desired antimicrobial effect that is desired. For example, when using octenidine dihydrochloride or an octenidine salt the concentration may vary from about 0.0001% w/v to about 4.0% w/v, more preferably from about 0.001% w/v to about 2.0% w/v, more preferably from about 0.01% w/v to about 0.5% w/v, and still more preferably from about 0.1% w/v to about 0.4% w/v. When chlorhexidine or a chlorhexidine salt is used, the concentration may be from about 0.1% w/v to about 4.0% w/v, more preferably from about 0.25% w/v to about 2.5% w/v, more preferably from about 0.5% w/v to about 2.25% w/v, and still more preferably about 1.2% w/v to about 2.0% w/v.

As shown in FIGS. 1-4, the applicator 100 also includes at least one actuator 160. The actuator 160 may include a dimple 162 having a shape congruent to a human thumb. The dimple 162 may include a plurality of ridges 164 to assist the user in locating the dimple and preventing slippage of the thumb during use. The actuator 160 may comprise any mechanism configured such that, when actuated, allows the user to fracture the ampoule 140 (or multiple ampoules if multiple ampoules are implemented). In an aspect of the present invention, the fracturing of the ampoules may be achieved via compressing the actuator 160 toward the body 110, which is described in more detail below. The actuator 160 may comprise a lever. As shown in FIGS. 1-4, the actuator 160 may project from a top portion of body 110. However, it will be appreciated that actuator 160 may project from any portion of body 110, such as a side portion, as long as it is aligned with ampoule 140. As best seen in FIGS. 1, 3, and 4, the actuator 160 may include a contact portion 152, which applies compressive force to the body 110 when the actuator 160 is actuated. The contact portion 152 may be aligned with the ampoule 140, or aligned with multiple ampoules when multiple ampoules are implemented.

The actuator 160, prior to actuation may extend at an angle 156 (FIGS. 3 and 4) toward the proximal end 112 of the body 110 (e.g., the free end of the actuator may be located closer to the proximal end of the body than the portion of the actuator connected to the body) such that when the actuator is actuated (i.e., pressed toward the body 110), the contact portion 152 applies compressive pressure to the body 110. The angle 156 may be from about 1° to about 60°, more preferably from about 5° to about 40°, more preferably from about 10° to about 30°, and still more preferably about 12° to about 18°. The actuation of the actuator 160 is described in more detail below.

With the ampoules 140 mounted in the body 110, as described above, and the application member 120 mounted to close off the distal end portion 130 of the body 110, a fluid chamber 170 (FIG. 4) may be formed that extends between the application member 120 and the ampoule 140. A fluid metering device, such as a pledget 180 (FIG. 4), for example, may be provided in the fluid chamber 170 to further control and/or direct the flow of solution from the ampoule 140 when the assembly 100 is in use. In accordance with another aspect of the present invention, the pledget 180 may tint the solution as the solution flows from the ampoule to the application member 120. In an aspect of the present invention, the pledget 180 may provide enhanced flow control and tinting of the solution as it flows from the ampoule 140 into the pledget 180. The pledget may comprise a polyolefin fiber matrix. In an aspect of the present invention, any suitable hydrophobic polymer material that allows for the flow of a hydroalcoholic solvent may be used. For example, the polymer may be a non-woven polyester.

The pledget 180 may have a dye incorporated therein so that the antiseptic solution becomes tinted as it passes through the pledget. Preferably, the impregnated dye is anionic in nature. The anionic dye may be any suitable dye approved by the FDA and international authorities for use in food, drugs, and/or cosmetics (e.g., D&C and FD&C dyes). Preferred dyes may be selected from the group consisting of FD&C Blue No. 1 (Brilliant Blue FCF), FD&C Blue No. 2 (Indigo Carmine), FD&C Green No. 3 (Fast Green FCF), FD&C Red No. 3 (Erythrosine), FD&C Red No. 40 (Allura Red), FD&C Yellow No. 5 (Tartrazine), FD&C Yellow No. 6 (Sunset Yellow FCF), D&C Yellow No. 8 (Fluorescein), D&C Orange No. 4, D&C Yellow 10 (Quinoline Yellow WS), D&C Yellow No. 11, D&C Red No. 30, and combinations thereof. Other suitable dyes include beta-carotene, curcumin, iron oxide yellow, and riboflavin, iron oxide red, chlorophyll, and the like. Two or more anionic dyes may also be combined and used together.

As shown in FIGS. 1 and 2, the applicator 100 may include a trench 190 formed through the body 110. The trench 190 may extend from the proximal end 112 to a point about midway between the proximal end 112 and the distal end 130. As best seen in FIG. 1, the trench 190 may terminate at a vent hole 192. The termination point may be positioned along the body such as underneath the actuator 160. The location may be chosen to best prevent the user from accidentally covering a vent hole 192. The vent 192 hole may be positioned at a surface 194 that extends transverse relatively to the length of the trench 190. With the vent hole 192 located at the surface 194, it is much harder for a user to accidentally cover the vent hole 194 when operating the device.

FIG. 5-7 show cross section views of the applicator at various points along the body 110. These cross section views show how the cross section shape of the body 110 varies along the length of the body 110. FIG. 5, taken along line 5-5 of FIG. 2, shows the cross section shape of the body 110 near the distal end of 130. As shown in FIG. 5, the body 110 has a substantially circular cross section at this point, but has a slight taper 111. FIG. 6, taken along line 6-6 of FIG. 2 shows the cross section shape of the body 110 near the proximal end 112. As shown in FIG. 6 the body 110 at this point has a taper 113 that is more sharply tapered than the taper 111 shown in FIG. 5. Other than the presence of trench 190 in the cross section, the body 110 has a substantially teardrop shape in FIG. 6. FIG. 7, taken along line 7-7 of FIG. 2 shows the cross section shape of the body 110 at the proximal end 112. As shown in FIG. 7, at the proximal end 112, the body 110 has become even more tapered as compared to the FIGS. 5 and 6 and has a substantially shield shape 115. Thus, the body 110 transitions from a substantially circular cross section shape to a substantially teardrop cross section shape to a substantially shield cross section shape from the distal end 130 to the proximal end 112. This arrangement of the body allows for enhanced ergonomics as compared to a body having a purely cylindrical shape.

Actuation of the assembly 100 will now be described with reference to FIGS. 1-4. Activation of the applicator 100 to release the solution and control the flow may be achieved by one handed actuation of the actuator 160. To operate the applicator 100, the operator first grasps the body 110. The user then places a thumb onto the actuator. As noted above the dimple 162 and the ridges 164 will assist the user to locate the proper placement of the thumb. That is, the user will be able to feel whether the thumb is in the proper place to actuate the actuator 160. While thumb actuation is described above, it should also be understood that the user may grip the actuator with the palm of the hand. FIGS. 1-4 show the location of the actuator prior to any actuation. Prior to actuation the actuator has an angle 156 relative to the body 110.

When the operator desires to release some or all of the fluid contained in the ampoule 140, the operator begins to compress the actuator 160 toward the body 110 by applying a compressive force onto the actuator 160. As the actuator 160 begins to move toward the body 110, the contact portion 152 begins to apply pressure on the body 110. This pressure then applies pressure on the ampoules 140. Once sufficient compressive force is imparted at the contact portion 152, the ampoule 140 fractures, thereby releasing flow of the fluid contained therein.

After rupturing the ampoules 140, the solution will drain from the ampoule 140 into the fluid chamber 170 under its own weight. After passing through the pledget 180 and becoming tinted (if a tint is present in the pledget), the fluid flow passes into the fluid chamber 170. The solution may then soak into, or otherwise flow through, the application member 120. The fluid chamber 170 may serve to accumulate and distribute the solution evenly over substantially the entire area of the application member 120. Once the application member 120 is engorged, for example, the solution may then be applied to a patient by wiping the distal surface of the application member 120 against the skin.

While one actuator and one ampoule have been described with respect to operation of the applicator, as noted above, it should be understood that the same principle of actuation may be applied to any number of actuators and ampoules to give the user a greater control over how much fluid is released. For example multiple ampoules may be present and the single actuator may be configured to rupture all of the ampoules. In another example, multiple separate actuators may be implemented where each actuator is configured to rupture one or more ampoules.

Figure 8:
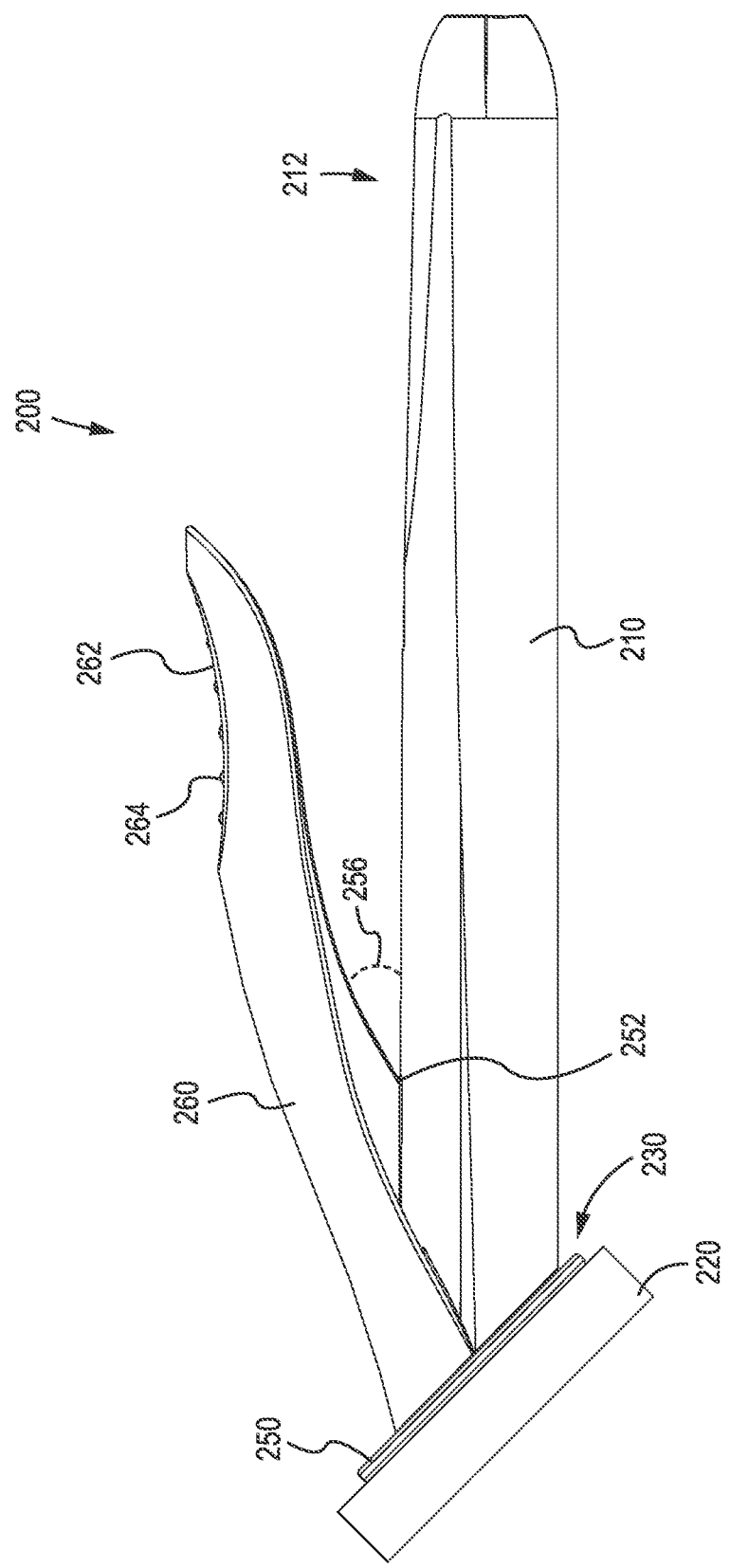
FIG. 8 is a side view of another embodiment of an antiseptic applicator assembly, in accordance with aspects of the present invention.
Figure 9:
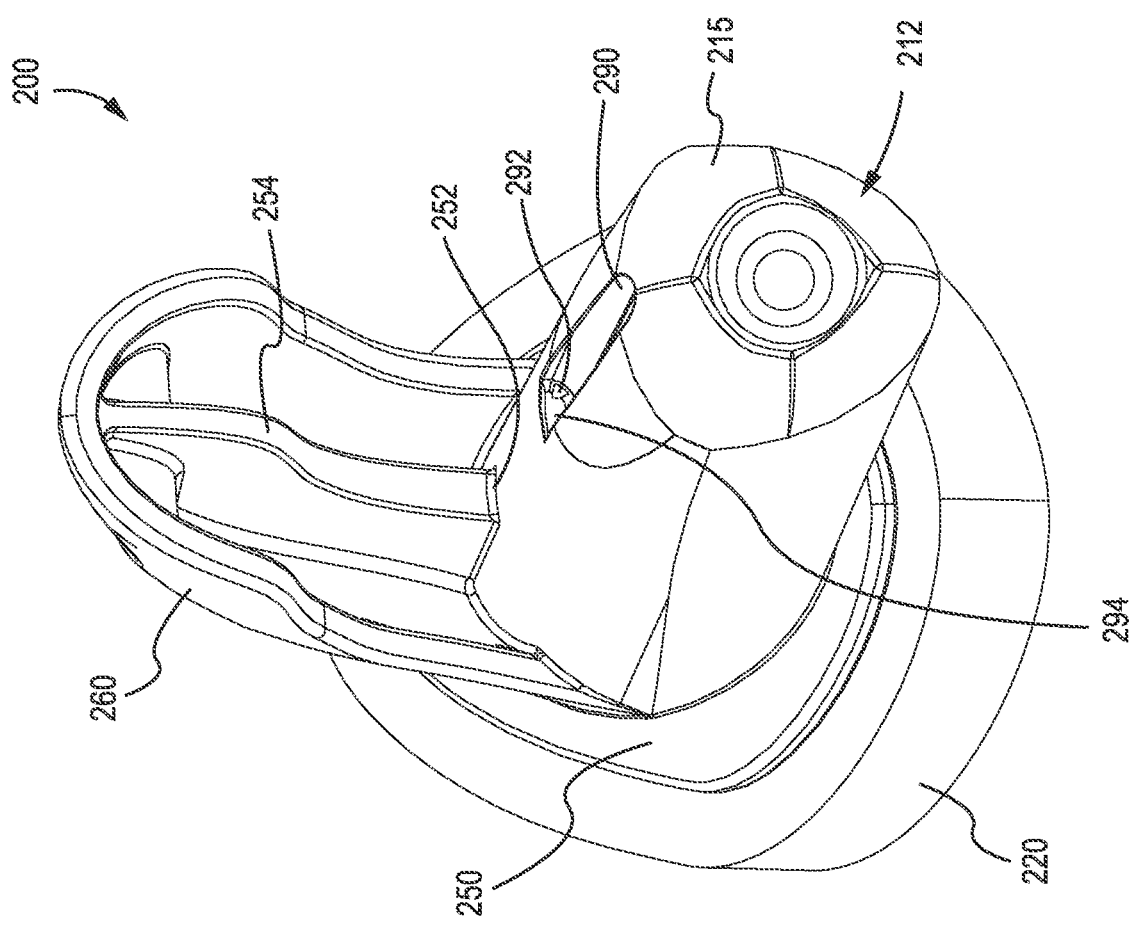
FIG. 9 is a rear perspective view of the antiseptic applicator assembly of FIG. 8.

FIGS. 8 and 9 show an applicator assembly 200 in accordance with other aspects of the present invention. The applicator assembly 200 is similar to the applicator assembly 100 discussed above and similar elements have similar reference numbers.

FIG. 8 shows a side view of the applicator assembly 200 prior to actuation to release fluid. FIG. 9 shows a rear perspective view of the applicator assembly 200. The antiseptic applicator assembly 200 may comprise a substantially hollow body 210, an application member 220 mounted to a distal end portion 230 of the body 210, and one or more ampoules received within the body 210. As shown in FIGS. 8 and 9, the application member 220 may have a teardrop shape. The internal components, e.g., the ampoule and pledget, of the applicator assembly 200 are not illustrated and may be the same as the internal components of applicator assembly 100 discussed above. Furthermore, the shape of the body 210 may be the same as the shape of the body 110, i.e., the cross section may transition to a shield shape 215. The application member 220 may be made as the same material as discussed above. The body 210 may include a mounting flange 250, as above.

The applicator 200 also includes an actuator 260. As shown in FIG. 8, the actuator 260 may similarly include a dimple 262 and ridges 264. As best seen in FIG. 8, the actuator 260 has been modified as compared to the actuator 160 of FIGS. 1-7. Specifically, the actuator 260 includes enhanced ergonomic aspects such as the shape of the dimple 262. The dimple 262 has been elongated and has a radius of curvature that more closely matches the contours of a human thumb. For example, the radius of curvature along the length of the dimple may vary depending on the overall size of the applicator assembly from about 1.60 inches to about 3.00 inches, more preferably from about out 1.75 inches to about 2.50 inches. Three particular examples of the radius of curvature along the length of the dimple are 1.75 inches, 2.10 inches, and 2.50 inches. Similarly, the ratio of the total length of the body to the radius of curvature along the length of the dimple may be from about 2.5:1 to about 4:1, more preferably about 3:1 to about 3.3:1. Three particular examples of the ratios include 3.02:1 (corresponding to the above example where the radius of curvature is 1.75 inches), 3.26:1 (corresponding to the above example where the radius of curvature is 2.10 inches), and 3.25:1 (corresponding to the above example where the radius of curvature is 2.50 inches). The length of the dimple may be about ⅙ to about ⅓ the length of the actuator, more preferably about ⅕ to about ¼ the length of the actuator, and most preferably about ¼ the length of the actuator. It should be noted that FIGS. 8 and 9 are drawn to scale, i.e., the figures illustrate the relative dimensions and curvatures of the various lines/portions relative to each other. As shown in FIGS. 8 and 9, the actuator 260 may comprise a lever. As shown in FIGS. 8 and 9 the actuator 260 may project from a top portion of body 210. However, it will be appreciated that actuator 260 may project from any portion of body 210 as long as it is aligned with the ampoule. As best seen in FIG. 9, the actuator 260 may include a contact portion 252 may apply a compressive force to the body 210 when the actuator 260 is actuated.

The actuator 260 also differs from the actuator 160 in the manner in which the actuator 260 contacts the body 210. As best seen in FIG. 9, the contact portion 252 is part of a rib structure 254 extending from an underside portion of the actuator 260. The rib structure 254 provides a larger area of contact 252 with the body 210 as compared to the applicator 160. When actuating the actuator 260 with compressive force the contact portion 252 provides a greater contact area on the body 210 which assists in rupturing the ampoule(s) contained in the body 210.

The actuator 260, prior to actuation may extend at an angle 256 (FIG. 8) toward the proximal end 212 of the body 210 (e.g., the free end of the actuator may be located closer to the proximal end of the body than the portion of the actuator connected to the body) such that when the actuator 260 is actuated (i.e., pressed toward the body 210), the contact portion 252 applies compressive pressure to the body 210. The angle 256 may be the same as discussed above.

With the ampoule mounted in the body 210, as described above, and the application member 220 mounted to close off the distal end portion 230 of the body 210, a fluid chamber (not shown, equivalent location as in applicator 100) may be formed that extends between the application member 220 and the ampoules. As noted above a fluid metering device, such as a pledget (not shown, equivalent location as in applicator 100), may be provided in the fluid chamber to further control and/or direct the flow of solution from the ampoules when the assembly 200 is in use. The pledget may be the same as discussed above. As shown in FIG. 9, the applicator 200 may include a trench 290 formed through the body 210. The trench 290 may be the same as discussed above including the vent hole 292 and the surface 294.

Actuation of the assembly 200 is the same as discussed above with respect to the assembly 100, except that in the case of the assembly 200, the entire contact portion 252 supported by the rib structure 254 acts upon the body 210. Further, as noted above, the ergonomically designed shape of the actuator 260 provides easier actuation for the user. After rupturing one or more of the ampoules, the solution will drain from the ampoule into the fluid chamber and may ultimately applied to the patient in the same manner as discussed above with respect to the applicator 100.

While one ampoule has been described, as noted above, it should be understood that as with the assembly 100, multiple ampoules may be implemented.

FIGS. 10-15 show an applicator assembly 300 in accordance with other aspects of the present invention. The applicator assembly 300 is similar to the applicator assembly 100 discussed above and similar elements have similar reference numbers.

Figure 10:
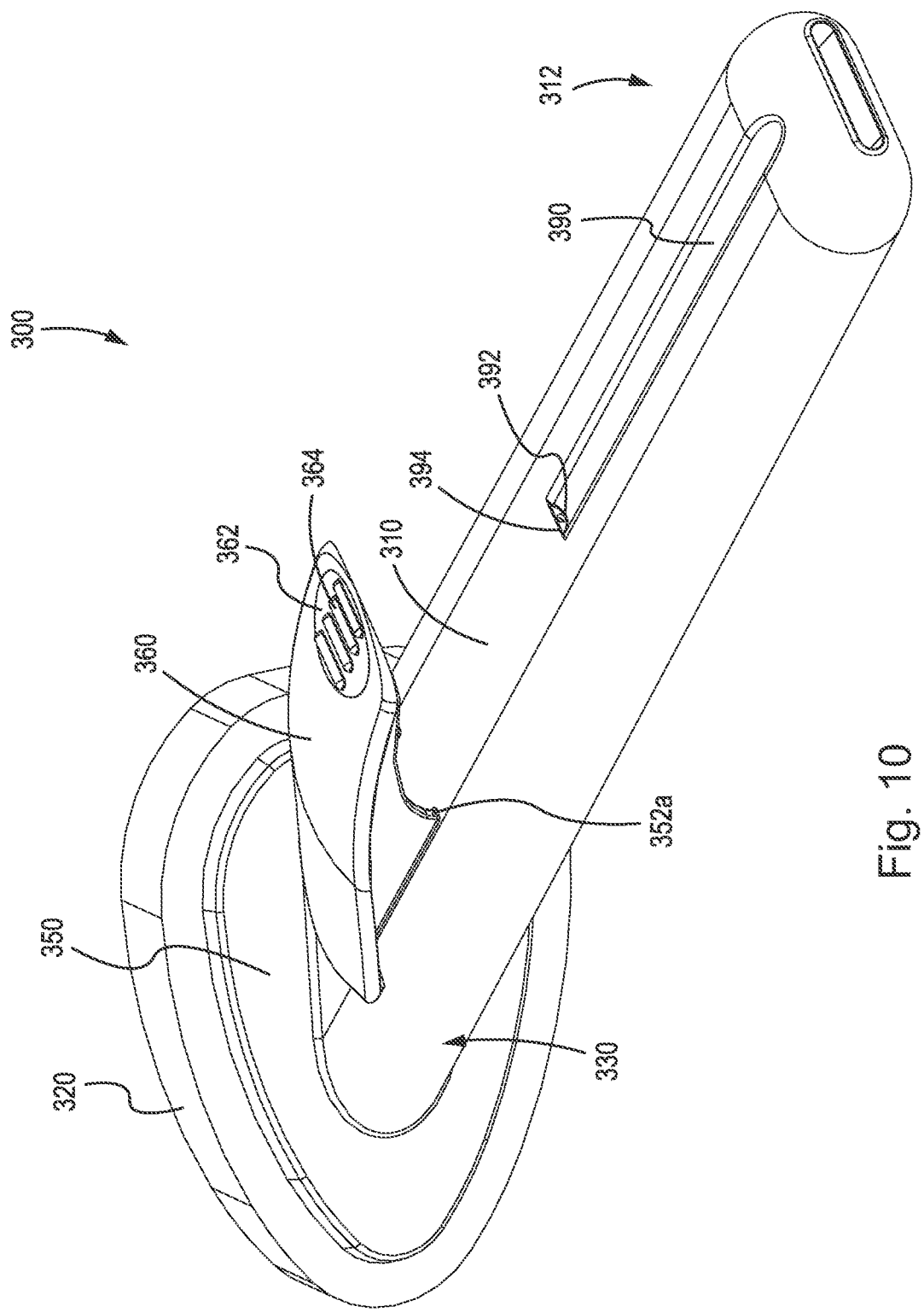
FIG. 10 is a perspective view of another embodiment of an antiseptic applicator assembly, in accordance with aspects of the present invention.
Figure 11:
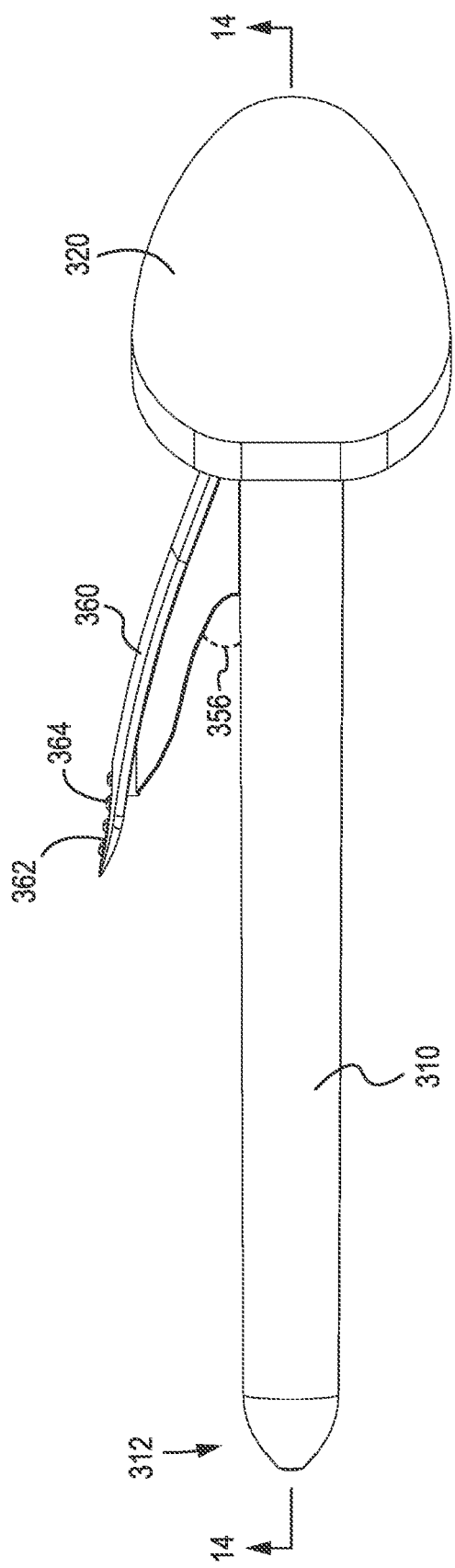
FIG. 11 is a bottom view of the antiseptic applicator assembly of FIG. 10.
Figure 12:
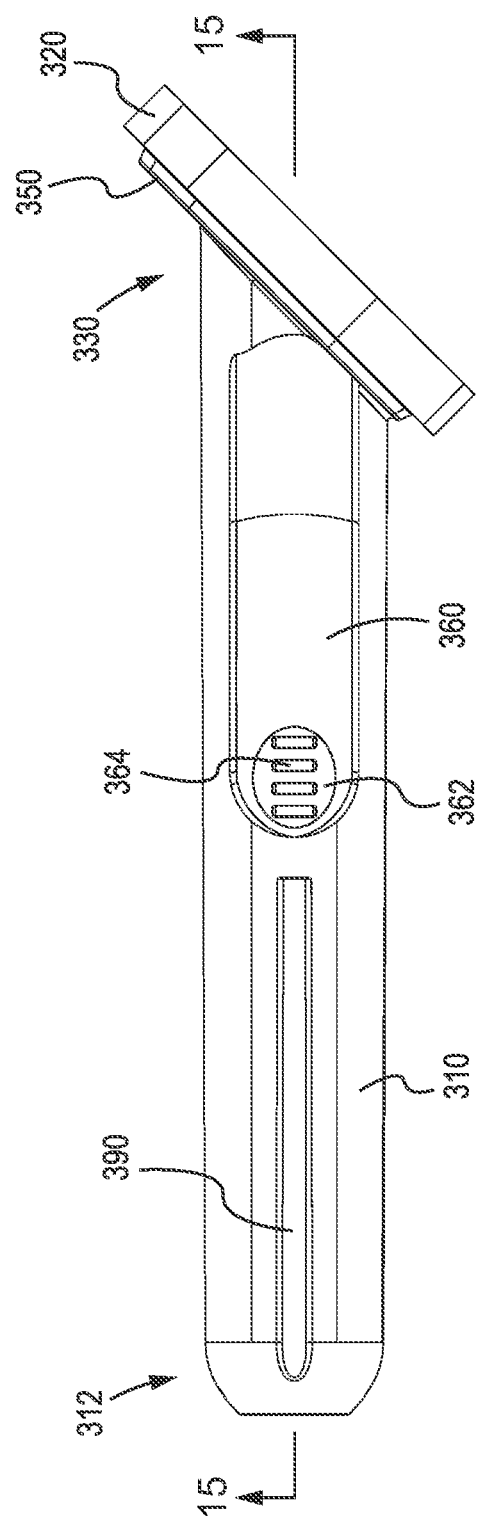
FIG. 12 is a side view of the antiseptic applicator assembly of FIG. 10.
Figure 13:
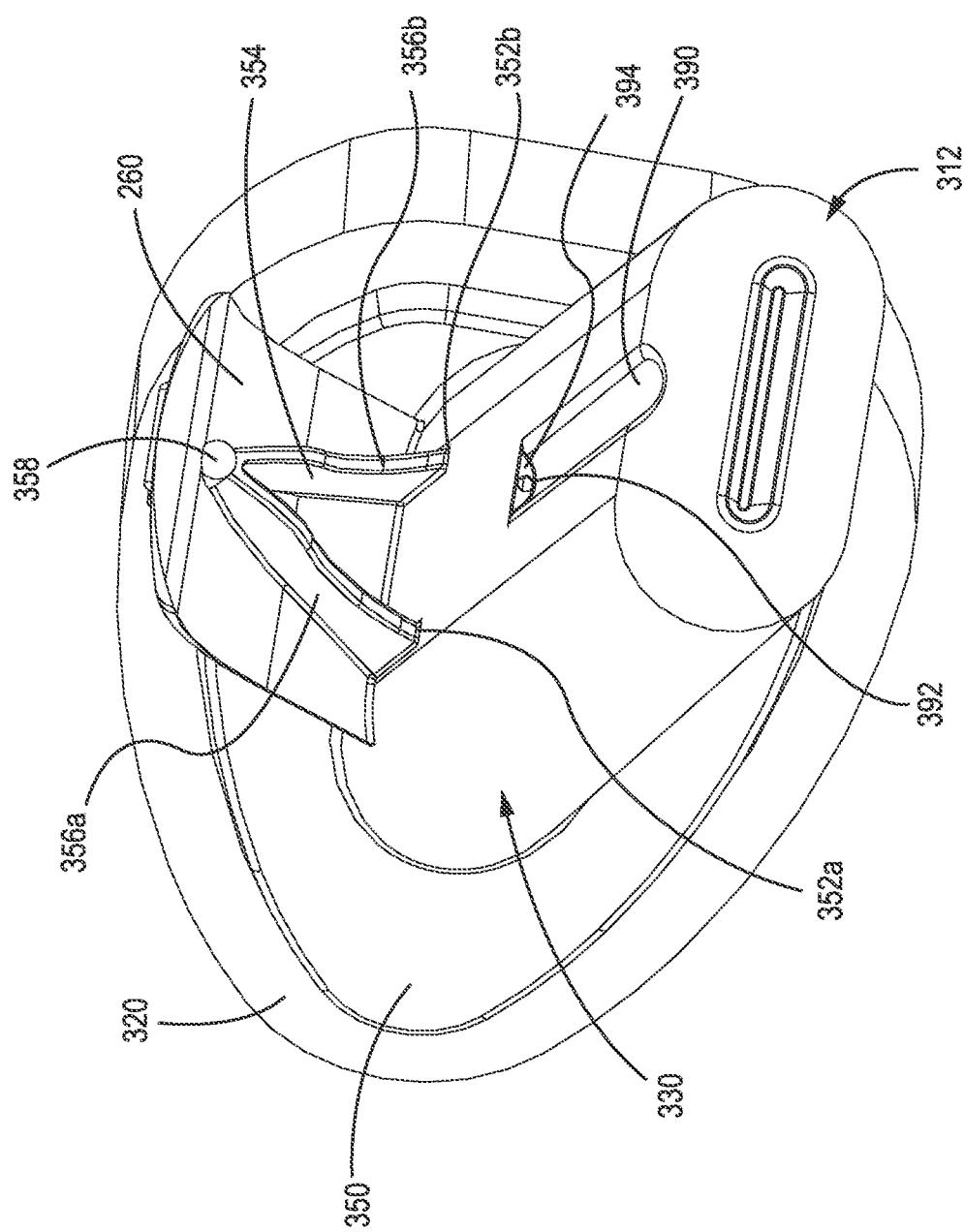
FIG. 13 is a rear perspective view of the antiseptic applicator assembly of FIG. 10.
Figure 14:
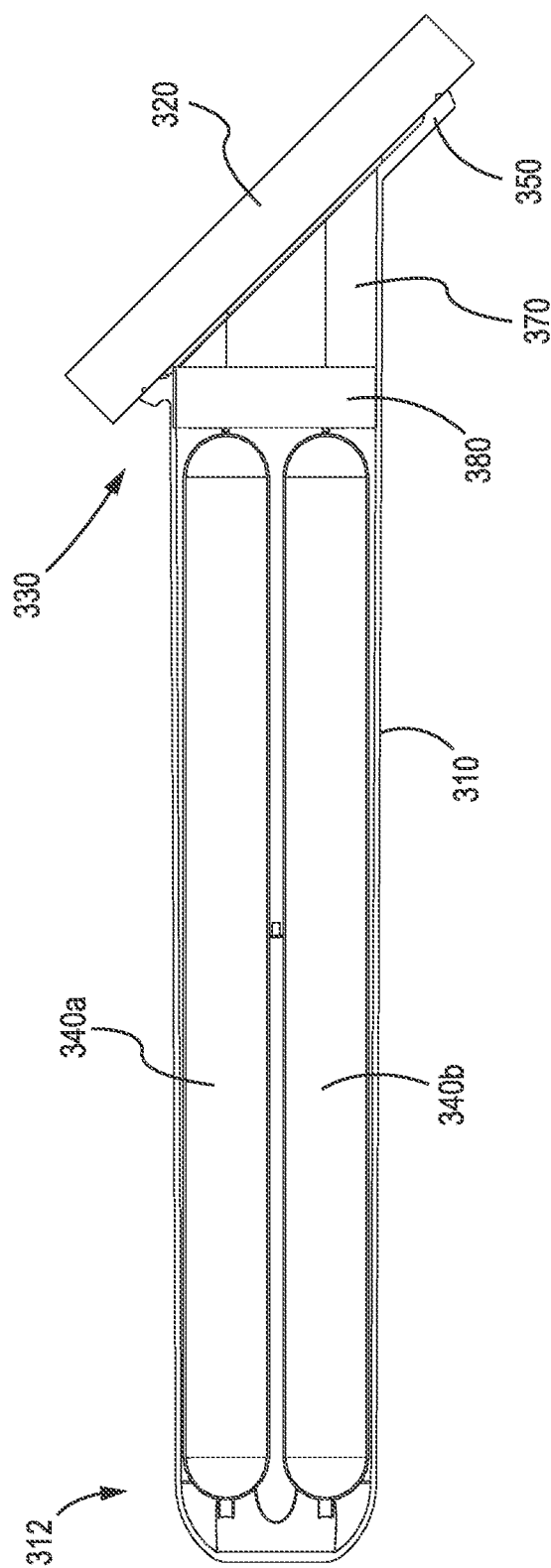
FIG. 14 is a cross sectional view of the antiseptic applicator assembly of FIG. 10 taken along line 14-14 of FIG. 11.
Figure 15:
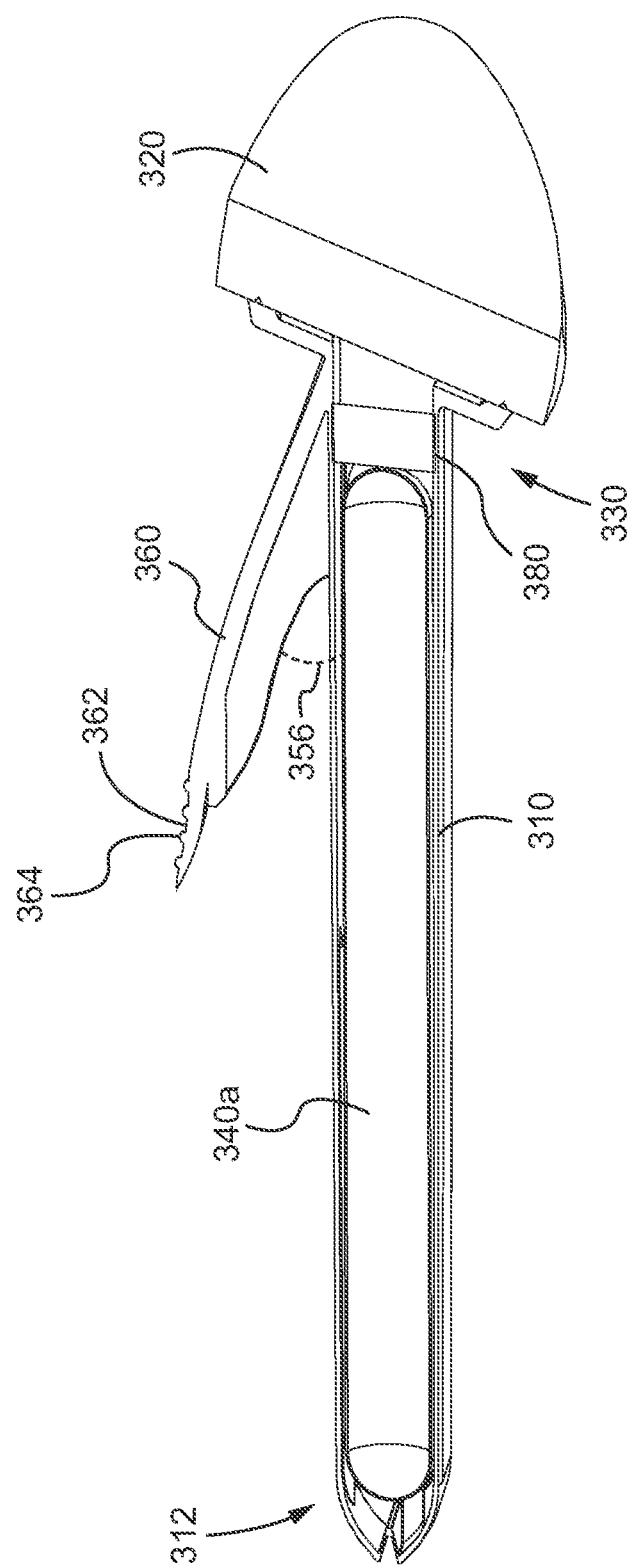
FIG. 15 is a cross sectional view of the antiseptic applicator assembly of FIG. 10 taken along line 15-15 of FIG. 12.

FIG. 10 shows a perspective view of the applicator assembly 300 prior to actuation to release fluid. FIG. 11 shows a bottom view of the applicator assembly 300. FIG. 12 shows a side view of the applicator assembly 300. FIG. 13 shows a rear perspective view of the applicator assembly 300. FIG. 14 shows a cross section of the applicator assembly 300 taken along line 14-14 of FIG. 11. FIG. 15 shows a cross section of the applicator assembly 300 take along line 15-15 of FIG. 12.

As shown in FIGS. 10-15, the antiseptic applicator assembly 300 may comprise a substantially hollow body 310, which may be oblong in shape, an application member 320 mounted to a distal end portion 330 of the body 310, and one or more ampoules 340a, 340b (FIGS. 14 and 15) received within the body 310. The ampoules may be the same as described above. The application member 320 may be made of the same material as discussed above and may have a teardrop shape. The body 310 may be configured to have a mounting flange 350 at the distal end portion, as discussed above.

As shown in FIGS. 10-13, the applicator 300 also includes an actuator 360. The actuator 360 may include a dimple 362 having a shape congruent to a human thumb. The dimple 362 may include a plurality of ridges 364 to assist the user in locating the dimple and preventing slippage of the thumb during use. The actuator 360 may comprise any mechanism configured such that, when actuated, allows the user to fracture the ampoules 340a, 340b (or a single ampoule). In an aspect of the present invention, the fracturing of the ampoules may be achieved via compressing the actuator 360 toward the body 310, which in the same manner as discussed above. The actuator 360 may comprise a lever.

As shown in FIGS. 10-13, the actuator 360 may project from a side portion of body 310. Thus, as best shown in FIG. 14, the ampoules may be vertically stacked relative to a longitudinal axis of the application member. However, it will be appreciated that actuator 360 may project from any portion of body 310, such as a top portion, as long as it is aligned with ampoules 340a, 340b. As best seen in FIG. 13, the actuator 360 may include contact points 352a, 352b, which apply compressive force to the body 310 when the actuator 360 is actuated. The contact points 352a, 352b may be aligned with the ampoules 340a, 340b, or aligned with a single ampoule if a single ampoule is implemented. As best seen in FIG. 13, the contact points 352a, 252b are part of a rib structure 354 extending from an underside portion of the actuator 360. The rib structure may include two angled ribs 356a, 356b that meet at a common point 358. Thus, as shown in FIG. 13, the rib structure may be in the form of a truss. The rib structure 254, forming the truss, provides enhanced structural support when applying compressive force on the contacts points 352a, 352b with the body 310 as compared to an applicator having two parallel ribs that do not form a truss.

The actuator 360, prior to actuation may extend at an angle 356 (FIGS. 11 and 15) toward the proximal end 312 of the body 310 (e.g., the free end of the actuator may be located closer to the proximal end of the body than the portion of the actuator connected to the body) such that when the actuator is actuated (i.e., pressed toward the body 310), the contact points 352a, 352b apply compressive pressure to the body 310. The angle 356 may be from about 1° to about 60°, more preferably from about 5° to about 40°, more preferably from about 10° to about 30°, and still more preferably about 12° to about 18°.

With the ampoules 340a, 340b mounted in the body 310, as described above, and the application member 320 mounted to close off the distal end portion 330 of the body 310, a fluid chamber 370 (FIG. 14) may be formed that extends between the application member 320 and the ampoules 340a, 340b. A fluid metering device, such as a pledget 380 (FIG. 14), for example, may be provided in the fluid chamber 370 to further control and/or direct the flow of solution from the ampoules 340a, 340b when the assembly 300 is in use. The pledget 380 may the same as discussed as above, including optionally being tinted.

As shown in FIGS. 10 and 13, the applicator 300 may include a trench 390 formed through the body 310. The trench 390 may extend from the proximal end 312 to a point about midway between the proximal end 312 and the distal end 330. As best seen in FIGS. 10 and 13, the trench 390 may terminate at a vent hole 392. The termination point may be positioned along the body such as underneath the actuator 360. The location may be chosen to best prevent the user from accidentally covering a vent hole 392. The vent 392 hole may be positioned at a surface 394 that extends transverse relatively to the length of the trench 390. With the vent hole 392 located at the surface 394, it is much harder for a user to accidentally cover the vent hole 394 when operating the device.

Actuation of the assembly 300 will now be described with reference to FIGS. 10-13, which is similar to the actuation process discussed above with respect to applicator assembly 100. Activation of the applicator 300 to release the solution and control the flow may be achieved by one handed actuation of the actuator 360. To operate the applicator 300, the operator first grasps the body 310. The user then places a thumb onto the actuator. As noted above the dimple 362 and the ridges 364 will assist the user to locate the proper placement of the thumb. That is, the user will be able to feel whether the thumb is in the proper place to actuate the actuator 360. While thumb actuation is described above, it should also be understood that the user may grip the actuator with the palm of the hand. When the operator desires to release the fluid contained in the ampoules 340a, 340b, the operator begins to compress the actuators 360 toward the body 310 by applying a compressive force onto the actuator 360. As the actuator 360 begins to move toward the body 310, the contact point 352a, 352b begin to apply pressure on the body 310. This pressure then applies pressure on the ampoules 340a, 340b. Once sufficient compressive force is imparted at the contact points 352a, 352b, the ampoules 340a, 340b fracture, thereby releasing flow of the fluid contained therein.

After rupturing the ampoules 340a, 340b, the solution will drain from the ampoules 340a, 340b into the fluid chamber 370 under its own weight. After passing through the pledget 380 and becoming tinted (if a tint is present in the pledget), the fluid flow passes into the fluid chamber 370. The solution may then soak into, or otherwise flow through, the application member 320. The fluid chamber 370 may serve to accumulate and distribute the solution evenly over substantially the entire area of the application member 320. Once the application member 320 is engorged, for example, the solution may then be applied to a patient by wiping the distal surface of the application member 320 against the skin.

While one actuator and two ampoules have been described with respect to operation of the applicator assembly 300, as noted above, it should be understood that the same principle of actuation may be applied to any number of actuators and ampoules. For example one ampoule or more than two ampoules may be present and the single actuator may be configured to rupture the ampoule(s). In another example, multiple separate actuators may be implemented where each actuator is configured to rupture one or more ampoules.

Figure 16:
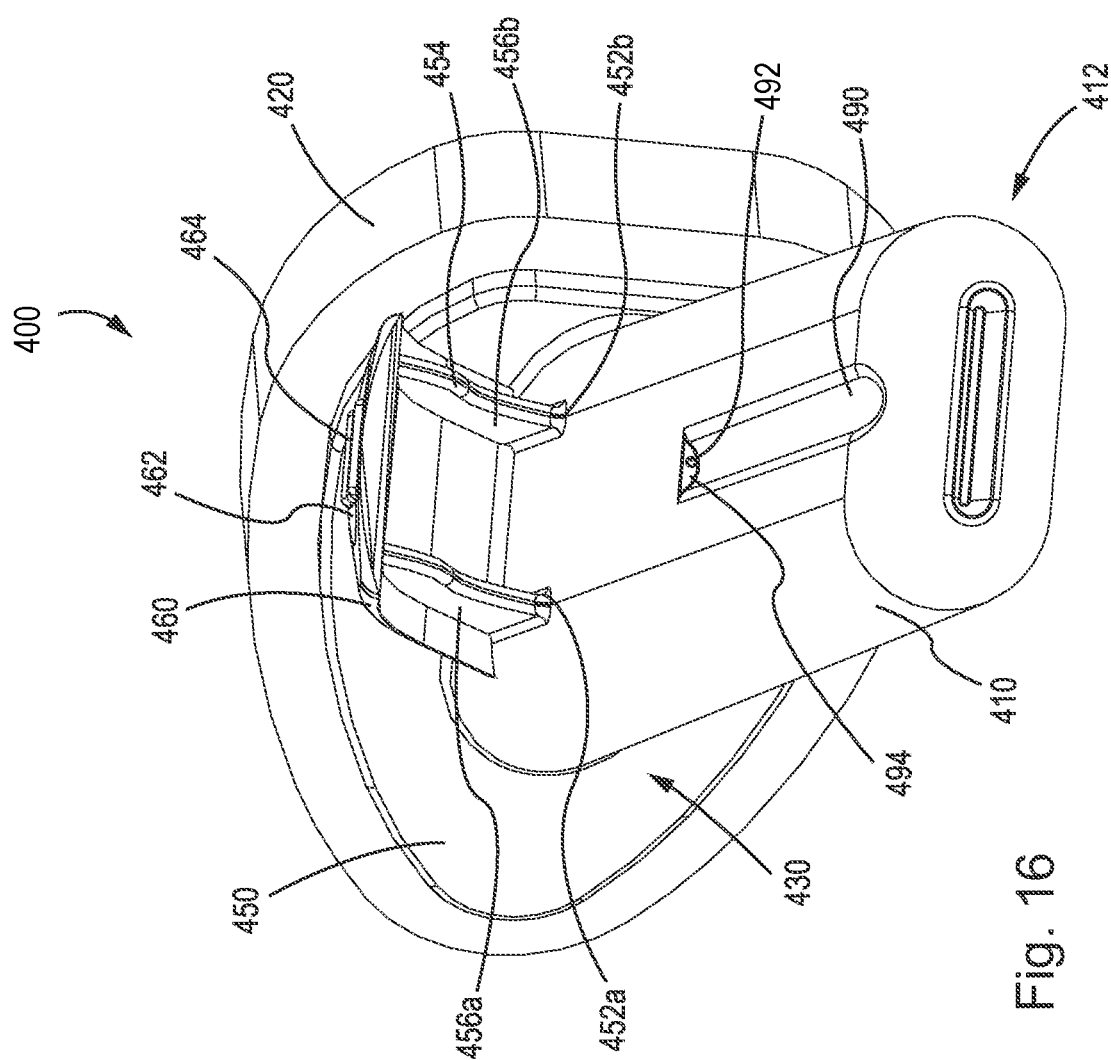
FIG. 16 is a rear perspective view of another embodiment of an antiseptic applicator assembly, in accordance with aspects of the present invention.

FIG. 16 shows a rear perspective view of an applicator assembly 400 in accordance with other aspects of the present invention. The applicator assembly 400 is similar to the applicator assembly 300 discussed above and similar elements have similar reference numbers. The antiseptic applicator assembly 400 may comprise a substantially hollow body 410, an application member 420 mounted to a distal end portion 430 of the body 410, and a plurality of ampoules received within the body 410. The internal components, e.g., the ampoules and pledget, of the applicator assembly 400 are not illustrated and would be the same as the internal components of applicator assembly 300 discussed above. The application member 420 may be made of the same material as discussed above and have a teardrop shape. The body 410 may include a mounting flange 450, as above.

The applicator also includes an actuator 460. The actuator 460 may include a dimple 462 having a shape congruent to a human thumb. The dimple 462 may include a plurality of ridges 464 to assist the user in locating the dimple and preventing slippage of the thumb during use. The actuator 460 may comprise any mechanism configured such that, when actuated, allows the user to fracture the ampoules (or a single ampoule). In an aspect of the present invention, the fracturing of the ampoules may be achieved via compressing the actuator 460 toward the body 410, which in the same manner as discussed above with respect to the applicator 300. The actuator 460 may comprise a lever.

As shown in FIG. 16, the actuator 460 may project from a side portion of body 410. Similar to the applicator assembly 300, the ampoules of the applicator assembly 400 may be vertically stacked relative to a longitudinal axis of the application member. However, it will be appreciated that actuator 460 may project from any portion of body 410, such as a top portion, as long as it is aligned with ampoules. The actuator 460 may include contact points 452a, 452b, which apply compressive force to the body 410 when the actuator 460 is actuated. The contact points 452a, 452b may be aligned with the ampoules. As shown in FIG. 16, the contact points 452a, 452b are part of a rib structure 454 extending from an underside portion of the actuator 460. The rib structure may include two parallel ribs 456a, 456b each terminating at one of the contact points 45a, 452b.

The actuator 460, prior to actuation may extend at an angle toward the proximal end 412 of the body 410 (e.g., the free end of the actuator may be located closer to the proximal end of the body than the portion of the actuator connected to the body) such that when the actuator is actuated (i.e., pressed toward the body 410), the contact points 452a, 452b apply compressive pressure to the body 410. The angle may be the same as discussed above with respect to the applicator assembly 300.

With the ampoules mounted in the body 410, as described above, and the application member 420 mounted to close off the distal end portion 430 of the body 410, a fluid chamber (not shown, in the same location as discussed above with respect to applicator assembly 300) may be formed that extends between the application member 420 and the ampoules. A fluid metering device, such as a pledget (not shown, in the same location as discussed above with respect to applicator assembly 300), for example, may be provided in the fluid chamber to further control and/or direct the flow of solution from the ampoules when the assembly 400 is in use. The pledget may the same as discussed as above, including optionally being tinted.

As shown in FIG. 16, the applicator 400 may include a trench 490 formed through the body 410. The trench 490 may extend from the proximal end 412 to a point about midway between the proximal end 412 and the distal end 430. The trench 490 may terminate at a vent hole 492. The termination point may be positioned along the body such as underneath the actuator 460. The location may be chosen to best prevent the user from accidentally covering a vent hole 492. The vent 492 hole may be positioned at a surface 494 that extends transverse relatively to the length of the trench 490. With the vent hole 492 located at the surface 494, it is much harder for a user to accidentally cover the vent hole 494 when operating the device.

Actuation of the assembly 400 will now be described, which is similar to the actuation process discussed above with respect to applicator assembly 100. Activation of the applicator 400 to release the solution and control the flow may be achieved by one handed actuation of the actuator 460. To operate the applicator 400, the operator first grasps the body 410. The user then places a thumb onto the actuator. As noted above the dimple 462 and the ridges 464 will assist the user to locate the proper placement of the thumb. That is, the user will be able to feel whether the thumb is in the proper place to actuate the actuator 460. While thumb actuation is described above, it should also be understood that the user may grip the actuator with the palm of the hand. When the operator desires to release the fluid contained in the ampoules, the operator begins to compress the actuators 460 toward the body 410 by applying a compressive force onto the actuator 460. As the actuator 460 begins to move toward the body 410, the contact point 452a, 452b begin to apply pressure on the body 410. This pressure then applies pressure on the ampoules. Once sufficient compressive force is imparted at the contact points 452a, 452b, the ampoules fracture, thereby releasing flow of the fluid contained therein.

After rupturing the ampoules, the solution will drain from the ampoules into the fluid chamber under its own weight. After passing through the pledget and becoming tinted (if a tint is present in the pledget), the fluid flow passes into the fluid chamber. The solution may then soak into, or otherwise flow through, the application member 420. The fluid chamber may serve to accumulate and distribute the solution evenly over substantially the entire area of the application member. Once the application member 420 is engorged, for example, the solution may then be applied to a patient by wiping the distal surface of the application member 420 against the skin.

While one actuator and two ampoules have been described with respect to operation of the applicator assembly 400, as noted above, it should be understood that the same principle of actuation may be applied to any number of actuators and ampoules. For example one ampoule or more than two ampoules may be present and the single actuator may be configured to rupture the ampoule(s). In another example, multiple separate actuators may be implemented where each actuator is configured to rupture one or more ampoules.

Figure 17:
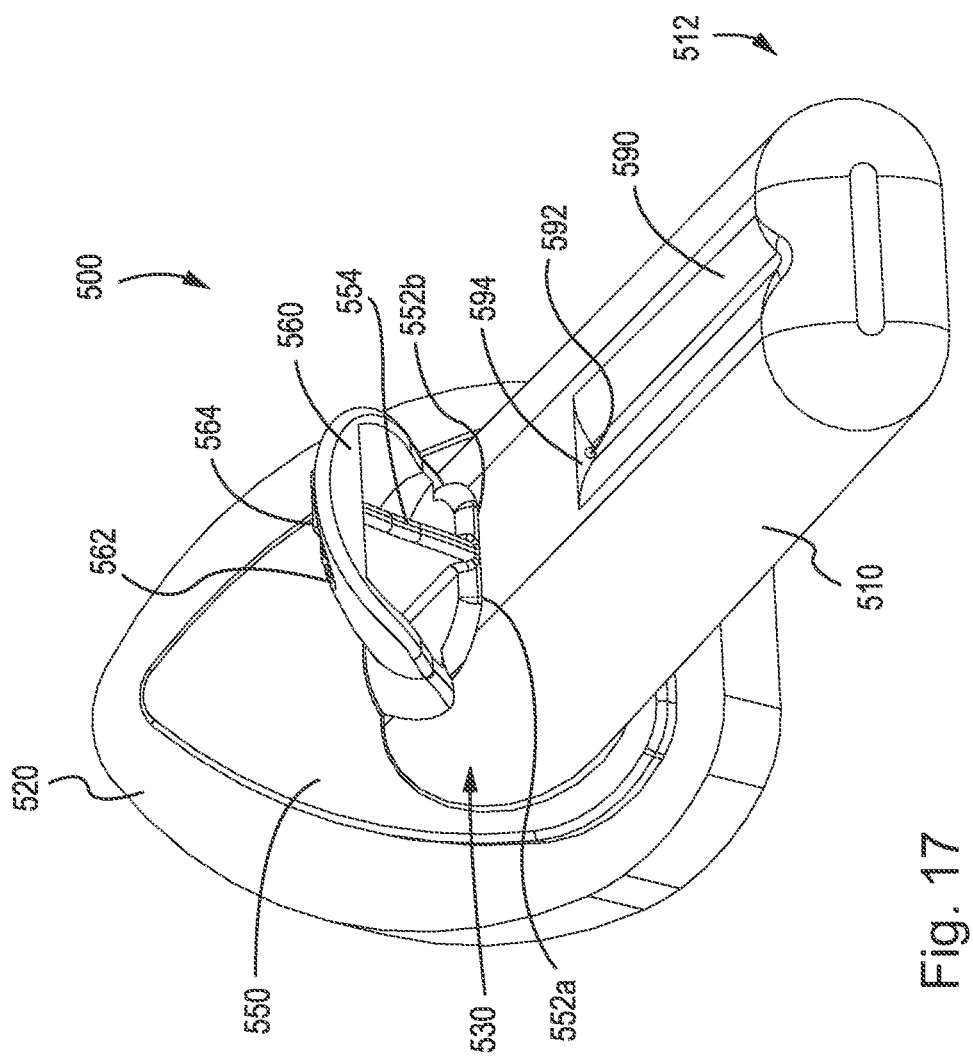
FIG. 17 is a rear perspective view of another embodiment of an antiseptic applicator assembly, in accordance with aspects of the present invention.

FIG. 17 shows a rear perspective view of an applicator assembly 500 in accordance with other aspects of the present invention. The applicator assembly 500 is similar to the applicator assembly 300 discussed above and similar elements have similar reference numbers. The applicator assembly 500 may comprise a substantially hollow body 510, an application member 520 mounted to a distal end portion 530 of the body 510, and a plurality of ampoules received within the body 510. The internal components, e.g., the ampoules and pledget, of the applicator assembly 500 are not illustrated and would be the same as the internal components of applicator assembly 300 discussed above. The application member 520 may be made as the same material as discussed above and may have a teardrop shape. The body 510 may include a mounting flange 550, as above.

The applicator also includes an actuator 560. The actuator 560 may include a dimple 562 having a shape congruent to a human thumb. The dimple 562 may include a plurality of ridges 564 to assist the user in locating the dimple and preventing slippage of the thumb during use. The actuator 560 may comprise any mechanism configured such that, when actuated, allows the user to fracture the ampoules (or a single ampoule). In an aspect of the present invention, fracturing of the ampoules may be achieved via compressing the actuator 560 toward the body 510, which in the same manner as discussed above with respect to the applicator 300. The actuator 560 may comprise a lever.

As shown in FIG. 17, the actuator 560 may project from a top portion of body 510. The ampoules of the applicator assembly 500 may be horizontally stacked relative to a longitudinal axis of the application member. However, it will be appreciated that actuator 560 may project from any portion of body 510, such as a side portion, as long as it is aligned with ampoules. The actuator 560 may include contact portions 552a, 552b, which apply compressive force to the body 510 when the actuator 560 is actuated. The contact portions 552a, 552b may be aligned with the ampoules. As shown in FIG. 17, the contact portions 552a, 552b may extend along the width of the body 510, thereby contacting a majority of the surface area of the body 510. Each of the contact portions 552a, 552b may be joined with a common rib structure 554 extending from an underside portion of the actuator 560. The rib structure 554 may extend approximately along the center of the actuator 560 and may join the contact portions 552a, 552b between the contact portions.

Because the contact portions 552a, 552b extend along the width of the body 510 and are connected to the rib structure 554, compressive force on the actuator 560 is distributed along the width of the body 510 via the contact portions 55a, 552b.

The actuator 560, prior to actuation may extend at an angle toward the proximal end 512 of the body 510 (e.g., the free end of the actuator may be located closer to the proximal end of the body than the portion of the actuator connected to the body) such that when the actuator is actuated (i.e., pressed toward the body 510), the contact portions 552a, 552b apply compressive pressure to the body 510. The angle may be the same as discussed above with respect to the applicator assembly 300.

With the ampoules mounted in the body 510, as described above, and the application member 520 mounted to close off the distal end portion 530 of the body 510, a fluid chamber (not shown, in the same location as discussed above with respect to applicator assembly 300) may be formed that extends between the application member 520 and the ampoules. A fluid metering device, such as a pledget (not shown, in the same location as discussed above with respect to applicator assembly 300), for example, may be provided in the fluid chamber to further control and/or direct the flow of solution from the ampoules when the assembly 500 is in use. The pledget may the same as discussed as above, including optionally being tinted.

As shown in FIG. 17, the applicator 500 may include a trench 590 formed through the body 510. The trench 590 may extend from the proximal end 512 to a point about midway between the proximal end 512 and the distal end 530. The trench 590 may terminate at a vent hole 592. The termination point may be positioned along the body such as underneath the actuator 460. The location may be chosen to best prevent the user from accidentally covering a vent hole 592. The vent 592 hole may be positioned at a surface 594 that extends transverse relatively to the length of the trench 590. With the vent hole 592 located at the surface 594, it is much harder for a user to accidentally cover the vent hole 494 when operating the device.

Actuation of the assembly 500 will now be described, which is similar to the actuation process discussed above with respect to applicator assembly 100. Activation of the applicator 500 to release the solution and control the flow may be achieved by one handed actuation of the actuator 560. To operate the applicator 500, the operator first grasps the body 510. The user then places a thumb onto the actuator. As noted above the dimple 562, and the ridges 564 will assist the user to locate the proper placement of the thumb. That is, the user will be able to feel whether the thumb is in the proper place to actuate the actuator 560. While thumb actuation is described above, it should also be understood that the user may grip the actuator with the palm of the hand. When the operator desires to release the fluid contained in the ampoules, the operator begins to compress the actuators 560 toward the body 510 by applying a compressive force onto the actuator 560. As the actuator 560 begins to move toward the body 510, the contact portions 52a, 552b begin to distribute the applied pressure along the width of the body 510. This pressure then applies pressure on the ampoules. Once sufficient compressive force is imparted at the contact portions 552a, 552b, the ampoules fracture, thereby releasing flow of the fluid contained therein.

After rupturing the ampoules, the solution will drain from the ampoules into the fluid chamber under its own weight. After passing through the pledget and becoming tinted (if a tint is present in the pledget), the fluid flow passes into the fluid chamber. The solution may then soak into, or otherwise flow through, the application member 520. The fluid chamber may serve to accumulate and distribute the solution evenly over substantially the entire area of the application member. Once the application member 520 is engorged, for example, the solution may then be applied to a patient by wiping the distal surface of the application member 520 against the skin.

While one actuator and two ampoules have been described with respect to operation of the applicator assembly 500, as noted above, it should be understood that the same principle of actuation may be applied to any number of actuators and ampoules. For example one ampoule or more than two ampoules may be present and the single actuator may be configured to rupture the ampoule(s). In another example, multiple separate actuators may be implemented where each actuator is configured to rupture one or more ampoules.

Figure 18:
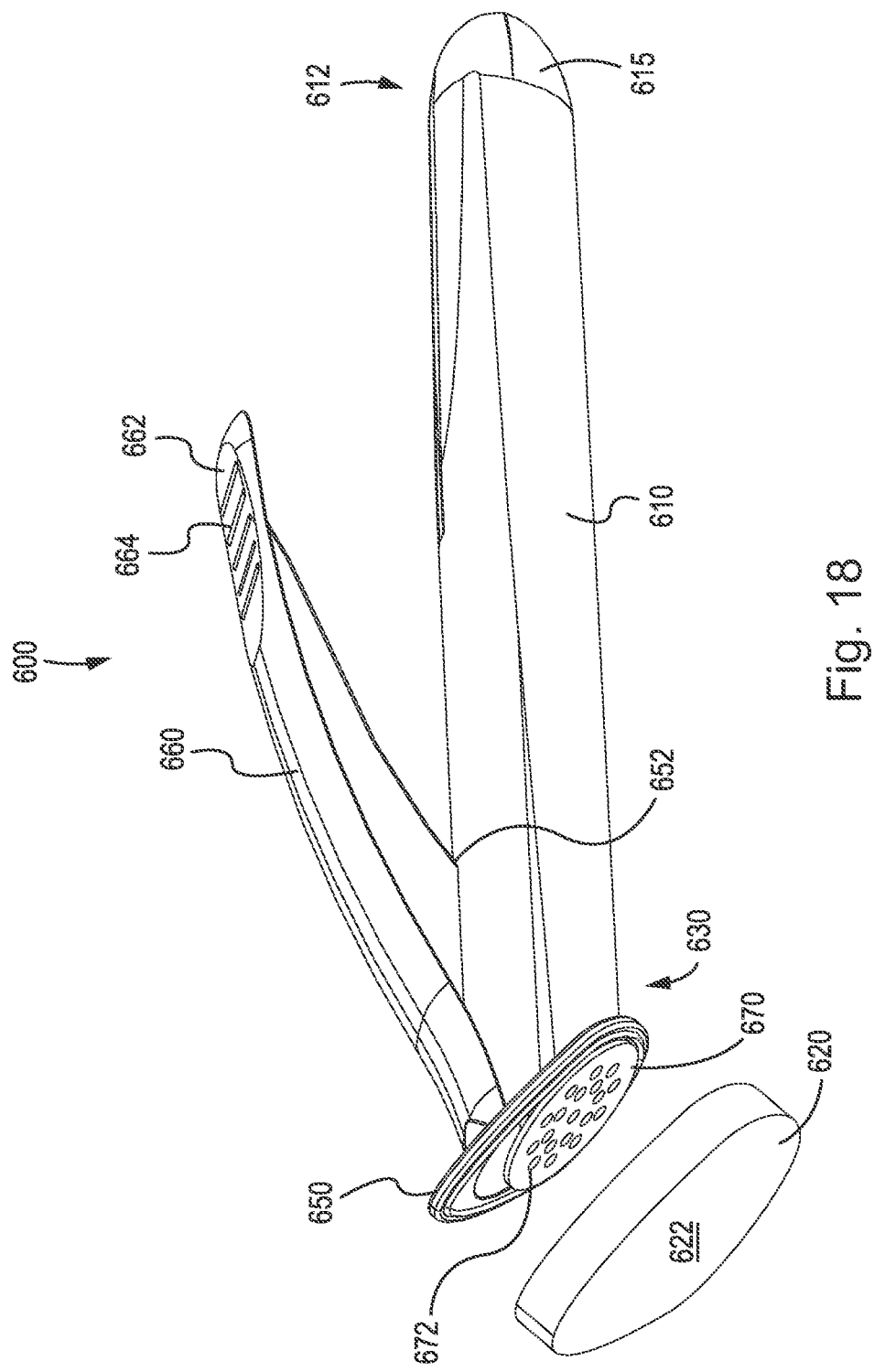
FIG. 18 is a partially exploded perspective view of another embodiment of an antiseptic applicator assembly, in accordance with aspects of the present invention.

FIG. 18 is a partially exploded perspective view of an applicator assembly 600 having a support grating 670. While the applicator assembly 600 is illustrated as having structure analogous to the applicator assembly 100, it should be understood that the additional features (i.e., the support grating) may be implemented in any of the above applicator assemblies.

The antiseptic applicator assembly 600 may comprise a substantially hollow body 610, an application member 620 mounted to a distal end portion 630 of the body 610, and one or more ampoules received within the body 610. As shown in FIG. 18, the application member 620 may have a teardrop shape. The internal components, e.g., the ampoule and pledget, of the applicator assembly 600 are not illustrated and would be the same as the internal components of applicator assembly 100 discussed above. Furthermore, the shape of the body 610 is the same as the shape of the body 110, i.e., the cross section may transition to shield shaped 615. However, as noted above, because the additional features of the applicator assembly 600 (i.e., the support grating) can be implemented in any of the above applicators, the body may have the same shape as any of the above described applicators. The application member 620 may be made as the same material as discussed above. The body 610 may include a mounting flange 650, as above.

The applicator 600 also includes an actuator 660. As shown in FIG. 18, the actuator 660 may similarly include a dimple 662 and ridges 664. The actuator 660 may comprise a lever. The actuator 660 may project from a top portion of body 610. However, it will be appreciated that actuator 660 may project from any portion of body 610 as long as it is aligned with the ampoule. The actuator 660 may include a contact portion 652 may apply a compressive force to the body 610 when the actuator 660 is actuated. The actuator 660, prior to actuation may extend at an angle toward the proximal end 612 of the body 610 (e.g., the free end of the actuator may be located closer to the proximal end of the body than the portion of the actuator connected to the body) such that when the actuator 660 is actuated (i.e., pressed toward the body 610), the contact portion 652 applies compressive pressure to the body 610. The angle may be the same as discussed above. While the actuator 660 is illustrated as being essentially the same as the actuator 160 of the applicator assembly 100, because the additional features of the applicator assembly 600 (i.e., the support grating) may be implemented in any of the above described applicator assemblies, the actuator 660 may be shaped and configured along with the body to operate as described above with respect to any of the applicator assemblies 100, 200, 300, 400, 500.

The applicator assembly 600 includes a support grating 670 disposed between the container 610 and the application member 620. As shown in FIG. 18, the support grating 670 may include a plurality of apertures 672. The plurality of apertures allows the antiseptic solution to flow through the support grating 670 and into the application member 620. The support grating 670 serves the function of adding additional support to the applicator when the operator is applying solution to a surface. Specifically, during operation, the operator presses the application member 620 against the surface so that the fluid soaked therein releases onto the surface. This pressure pushes the spongy foam material of the application member 620 rearward. The central area of the application member 620 (i.e., the area not welded to the flange 650) foam tends to retain more antiseptic liquid. The support grating 670 provides a contact surface area for the inner surface (i.e., the surface facing the body 610) of the application member 620. In particular, the support grating 670 provides a contact area at a central area of the inner surface of the application member 620 when the operator is pressing the outer surface 622 of the application member 620 against the skin. Thus, the support grating 670 will ensure a greater contact area of the inner surface of the application member as compared to an applicator without the support grating, which creates uniform pressure across the application member 620, and ultimately results in less residual volume of antiseptic solution left behind after the application of solution to the surface.

Figure 19:
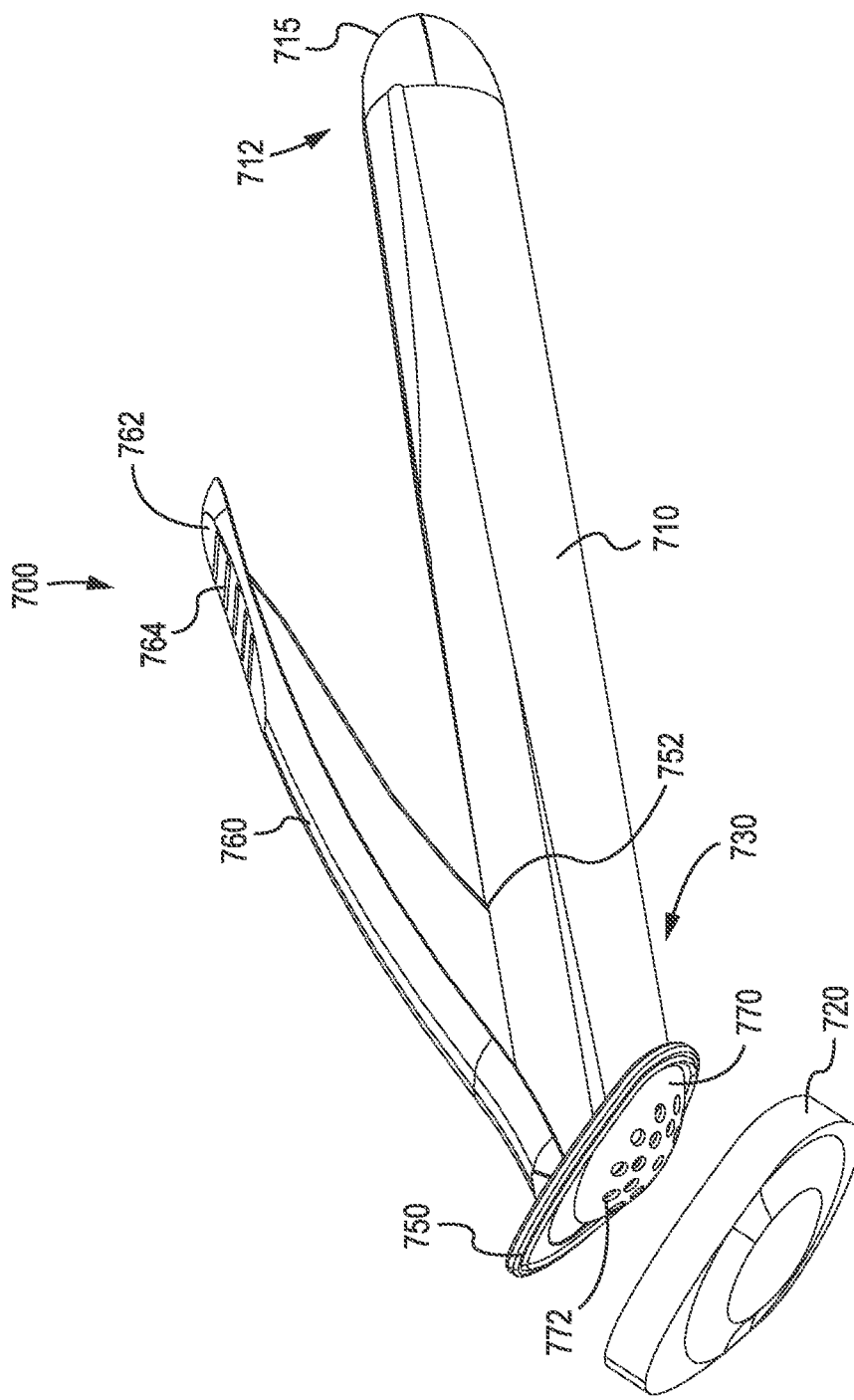
FIG. 19 is a partially exploded perspective view of another embodiment of an antiseptic applicator assembly, in accordance with aspects of the present invention.

FIG. 19 is an exploded perspective view of an applicator assembly 700 having another support grating 770. While the applicator assembly 700 is illustrated as having structure analogous to the applicator assembly 100, it should be understood that the additional features (i.e., the support grating) may be implemented in any of the above-described applicator assemblies.

The antiseptic applicator assembly 700 may comprise a substantially hollow body 710, an application member 720 mounted to a distal end portion 730 of the body 710, and one or more ampoules received within the body 710. As shown in FIG. 19, the application member 720 may have a teardrop shape. The internal components, e.g., the ampoule and pledget, of the applicator assembly 700 are not illustrated and would be the same as the internal components of applicator assembly 100 discussed above. Furthermore, the shape of the body 710 is the same as the shape of the body 110, i.e., the cross section may transition to shield shaped 715. However, as noted above, because the additional features of the applicator assembly 700 (i.e., the support grating) can be implemented in any of the above applicators, the body may have the same shape as any of the above described applicators. The application member 720 may be made as the same material as discussed above. The body 710 may include a mounting flange 750, as above.

The applicator 700 also includes an actuator 760. As shown in FIG. 19, the actuator 760 may similarly include a dimple 762 and ridges 764. The actuator 760 may comprise a lever. The actuator 760 may project from a top portion of body 710. However, it will be appreciated that actuator 760 may project from any portion of body 710 as long as it is aligned with the ampoule. The actuator 760 may include a contact portion 752 may apply a compressive force to the body 710 when the actuator 760 is actuated. The actuator 760, prior to actuation may extend at an angle toward the proximal end 712 of the body 710 (e.g., the free end of the actuator may be located closer to the proximal end of the body than the portion of the actuator connected to the body) such that when the actuator 760 is actuated (i.e., pressed toward the body 710), the contact portion 752 applies compressive pressure to the body 710. The angle may be the same as discussed above. While the actuator 760 is essentially the same as the actuator 160 of the applicator assembly 100, as noted above, because the additional features of the applicator assembly 700 (i.e., the support grating) may be implemented in any of the above described applicator assemblies, the actuator 760 may be shaped and configured along with the body to operate as described above with respect to any of the applicator assemblies 100, 200, 300, 400, 500.

The applicator assembly 700 additionally includes a support grating 770 disposed between the container 710 and the application member 720. As shown in FIG. 19, the support grating 770 may include a plurality of apertures 772. The plurality of apertures 772 allows the antiseptic solution to flow through the support grating 770 and into the application member 720. As shown in FIG. 19, the support grating 770 may have convex surface. Similarly, the application member 720 may have a congruently shaped surface so that the convex surface of the support grating 770 mates with the application member 720. The support grating 770 serves the same function as discussed above with respect with to the support grating 670. Additionally, because the support grating 770 is convex and the application member being congruently shaped, solution flowing through the support grating 770 and the application member is more easily applied to areas of the application surface that are not flat or convex shaped. For example, the convex shape of support grating 770 may be particularly well suited for concave or curved surfaces, such as an arm pit or inguinal area.

FIG. 20 shows a perspective view of an alternative embodiment of an application member 820. The application member 820 may be implemented in any of the applicator assemblies 100, 200, 300, 400, 500 discussed above. The application member 820 includes a support grating 870 extending from an inner surface 824 of the application member 820. As noted above, the inner surface 824 is the surface that that faces the body of the applicator assembly (i.e., the surface opposite the surface that is applied to the skin during use). The support grating 870 may be a separate material secured (e.g., by welding) to the surface 824. Alternatively, the support grating 870 may be the same material as the application member 820 such that it is integrally formed with application member 820. As shown in FIG. 20, the support grating 870 may form a plurality of openings 872 for allowing fluid flow. By having the support grating 870 formed on the surface 824 of the application member 820, it is not necessary to have a separate support grating as shown in the applicator assemblies 600, 700. The support grating 870 serves the same function of the support gratings 670, 770 as discussed above.

Thus, as above-described and shown in the FIGS. 18-20, the support gratings provides a firm and uniform contact between the applicator foam head and the application site, enhanced delivery of antiseptic solution, improved scrubbing action and increased penetration of drug products into upper layers of skin. While, round apertures are illustrated in FIGS. 18 and 19, the support grating can have a flat construction with apertures of various dimensions and shapes (e.g., square, rectangle, etc.). In another example aspect, the apertures may define a honeycomb construction with flat or rounded grids. The construction can be an independent structure to be assembled between the applicator tip and the foam head (e.g., FIGS. 18 and 19), can be an integrated structure molded into the application member (e.g., FIG. 20), or can be a part of the application member where the support grid is adhered onto the inner surface of the foams or adhered between two thin slices of foam application member material.

Various aspects of the present invention have been illustrated as distinct embodiments for clarity. While some features have already been described above as being applicable to other embodiments, it should be understood that all non-mutually exclusive features may be present throughout all of the illustrated embodiments. For example, the enhanced ergonomic features of the actuator 260 may be implemented in all of the other illustrated actuator assemblies.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but is to be accorded the full scope consistent with the language claims, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. An applicator assembly comprising:
   at least one ampoule formed of a frangible material and containing liquid to be applied;
   a body having a proximal end, a distal end, and an interior portion defining a chamber adapted to receive the at least one ampoule;
   an application member attached to the distal end of the body;
   an actuator projecting from the body operable to fracture the at least one ampoule;
   a trench formed in a surface of the body; and
   a vent extending through the trench,
   wherein the trench is at least partially defined by a wall extending transversely relative to a longitudinal axis of the body, and wherein the vent extends through the transverse wall and is in direct communication with an outside environment.

2. The applicator assembly of claim 1, wherein the trench extends from the proximal end of the body to about midway between the proximal end and the distal end.

3. The applicator assembly of claim 1, wherein the proximal end of the body comprises a non-circular cross section.

4. The applicator assembly of claim 1, wherein the proximal end of the body comprises a shield-shaped cross section.

5. The applicator assembly of claim 1, wherein the actuator comprises a dimpled portion shaped to match the contour of a human thumb.

6. The applicator assembly of claim 5, wherein the actuator comprises one or more ridges disposed in the dimpled portion.

7. The applicator assembly of claim 1, wherein the application member comprises a teardrop shape.

8. The applicator assembly of claim 1, wherein the applicator assembly comprises two ampoules, and wherein the two ampoules are stacked vertically relative to a longitudinal axis of the application member.

9. The applicator assembly of claim 1, wherein the applicator assembly comprises two ampoules, and wherein the two ampoules are stacked horizontally relative to a longitudinal axis of the application member.

10. The applicator assembly of claim 1, wherein the actuator comprises two ribs, each of the ribs having a first end in contact with the body and an opposing second end, and wherein the second ends are joined together.

11. The applicator assembly of claim 10, wherein the ribs form a truss.

12. The applicator assembly of claim 1, wherein the actuator comprises a rib having a first end in contact with the body, and contact portions extending from the rib along a surface of the body.

13. The applicator assembly of claim 1, wherein the actuator comprises a rib having a contact portion extending along a width of the body.

14. The applicator assembly of claim 1, wherein the actuator comprises two ribs, each of the ribs having an end in contact with the body, and wherein the two ribs extend substantially parallel to each other.

15. The applicator assembly of claim 1, further comprising a support grating disposed between the body and the application member.

16. The applicator assembly of claim 15, wherein the support grating comprises a convex surface and the application member comprises a congruently shaped surface.

17. The applicator assembly of claim 15, wherein the support grating is in contact with the application member.

18. The applicator assembly of claim 1, wherein the application member comprises a support grating extending from a surface of the application member.

\* \* \* \* \*